(12) United States Patent
Ritchart et al.

(10) Patent No.: US 11,083,460 B2
(45) Date of Patent: Aug. 10, 2021

(54) FIXATION OF VESSELS FOR PERCUTANEOUS FISTULA CREATION

(71) Applicant: Avenu Medical, Inc., San Juan Capistrano, CA (US)

(72) Inventors: Mark A. Ritchart, Dana Point, CA (US); Brad M. Kellerman, Escondido, CA (US); Justin K. Mann, Lake Elsinore, CA (US); Gene B. Reu, San Clemente, CA (US)

(73) Assignee: Avenu Medical, Inc., San Juan Capistrano, CA (US)

(*) Notice: Subject to any disclaimer, the term of this patent is extended or adjusted under 35 U.S.C. 154(b) by 27 days.

(21) Appl. No.: 16/530,848

(22) Filed: Aug. 2, 2019

(65) Prior Publication Data

US 2020/0038026 A1 Feb. 6, 2020

Related U.S. Application Data

(60) Provisional application No. 62/714,558, filed on Aug. 3, 2018.

(51) Int. Cl.
*A61B 17/11* (2006.01)
*A61B 17/12* (2006.01)
*A61B 17/00* (2006.01)

(52) U.S. Cl.
CPC ........ *A61B 17/11* (2013.01); *A61B 17/12109* (2013.01); *A61B 2017/00327* (2013.01); *A61B 2017/00584* (2013.01); *A61B 2017/00641* (2013.01); *A61B 2017/00663* (2013.01);
(Continued)

(58) Field of Classification Search
CPC . A61B 17/11; A61B 17/1103; A61B 17/1107; A61B 2017/1139; A61B 2017/00641; A61B 2017/00327; A61B 2017/00663; A61B 2017/1125; A61B 17/12109; A61B 2017/00606
See application file for complete search history.

(56) References Cited

U.S. PATENT DOCUMENTS 5,336,231 A * 8/1994 Adair ............... A61B 17/12013
 606/148
5,755,779 A 5/1998 Horiguchi
6,464,665 B1 10/2002 Heuser
(Continued)

FOREIGN PATENT DOCUMENTS

WO 2017124060 A1 7/2017

OTHER PUBLICATIONS

International Search Report and Written Opinion dated Oct. 29, 2019 for corresponding PCT App. No. PCT/US19/44968.

*Primary Examiner* — Diane D Yabut
*Assistant Examiner* — Christina C Lauer
(74) *Attorney, Agent, or Firm* — Stinson LLP

(57) ABSTRACT

A method of percutaneously creating a fistula includes inserting percutaneously a medical instrument to a target location having a first blood vessel and a second blood vessel. A fastener is then deployed via the medical instrument to the target location. The fastener is in a first configuration before the deploying and a second configuration after the deploying. The fastener limits relative movement between the first blood vessel and the second blood vessel when in the second configuration. An anastomosis between the first blood vessel and the second blood vessel is percutaneously produced.

14 Claims, 27 Drawing Sheets

(52) U.S. Cl.
CPC ............... *A61B 2017/00867* (2013.01); *A61B 2017/1107* (2013.01); *A61B 2017/1125* (2013.01)

(56) References Cited

U.S. PATENT DOCUMENTS

| | | |
|---|---|---|
| 6,638,257 B2 | 10/2003 | Amplatz |
| 8,062,321 B2 | 11/2011 | Heuser et al. |
| 9,138,230 B1 | 9/2015 | Buelna |
| 9,259,340 B2 | 2/2016 | Heuser et al. |
| 9,301,830 B2 | 4/2016 | Heuser et al. |
| 9,439,710 B2 | 9/2016 | Reu et al. |
| 9,439,728 B2 | 9/2016 | Hull et al. |
| 9,452,015 B2 | 9/2016 | Kellerman et al. |
| 9,474,562 B2 | 10/2016 | Kellerman et al. |
| 9,486,276 B2 | 11/2016 | Rios et al. |
| 9,522,016 B2 | 12/2016 | Kellerman et al. |
| 10,045,817 B2 | 8/2018 | Miller et al. |
| 10,070,866 B1 | 9/2018 | Kellerman et al. |
| 2003/0229363 A1* | 12/2003 | Sharkawy ............... A61B 17/11 606/153 |
| 2007/0203515 A1 | 8/2007 | Heuser et al. |
| 2010/0022940 A1 | 1/2010 | Thompson |
| 2010/0099947 A1 | 4/2010 | Sato et al. |
| 2011/0306959 A1 | 12/2011 | Kellerman et al. |
| 2013/0274648 A1 | 10/2013 | Weinberger |
| 2015/0196705 A1 | 7/2015 | Brenneman et al. |
| 2015/0297818 A1 | 10/2015 | Matsubara et al. |
| 2017/0119464 A1 | 5/2017 | Rios et al. |
| 2018/0206845 A1 | 7/2018 | Brenneman et al. |

\* cited by examiner

FIXATION OF VESSELS FOR PERCUTANEOUS FISTULA CREATION

CROSS-REFERENCE TO RELATED APPLICATIONS

This application claims benefit of priority to U.S. Provisional Application Ser. No. 62/714,558 entitled Fixation of Vessels for Percutaneous Fistula Creation, filed Aug. 3, 2018, which is expressly incorporated herein by reference in its entirety.

BACKGROUND

Vascular access is the lifeline supporting patients with end stage kidney disease. Traditionally, patients have had three different choices for vascular access—central catheter, graft, or surgically created autogenous fistula. Clinical research has shown that an autogenous fistula provides the best long-term clinical result, so it is the preferred method for vascular access. A vascular surgeon carefully dissects an appropriate vein and anastomoses it to a nearby artery to create a fistula. The surgically created fistula significantly increases the blood flow in the vein, causing an increase in diameter and thickness so that it can be used for dialysis access. Kidney Disease Outcomes Quality Initiative (KDOQI) guidelines suggest that the anastomosis is created as distal as the vasculature will support to maximize the amount of vein available for dialysis access.

Percutaneously created anastomoses are a new medical advancement in recent years. Percutaneous methods are disclosed, for example, in U.S. Pat. No. 9,439,710 entitled Intravascular Arterial to Venous Anastomosis and Tissue Welding Catheter, which is expressly incorporated by reference in its entirety. Such percutaneous methods eliminate the need to surgically dissect the vein, suture it to the artery. Although clinical trials have shown positive results with fistulas created percutaneously, known methods are often limited to creating an upper arm fistula due to anatomical limitations. The main anatomical limitation is that the vessels need to be within close proximity to one another (<2 mm) and in the same vascular bundle. If there is too much interstitial tissue causing a distracting force or independent movement between the vessels, currently available systems may be unable to fuse the vessels together, which may lead to an aneurismal sac between the artery and the vein or uncontrolled bleeding.

Thus, a need exists for improved methods and devices for fixing targeted vessels together or limiting relative motion between targeted vessels.

SUMMARY OF THE INVENTION

The present invention provides innovative systems, devices, and methods for enabling the fixation of two vessels together which are in separate tissue planes or vascular bundles, so that an anastomosis can be percutaneously created between them.

In some embodiments, a method of percutaneously creating a fistula includes inserting percutaneously a medical instrument to a target location having a first blood vessel and a second blood vessel. A fastener is then deployed via the medical instrument to the target location. The fastener is in a first configuration before the deploying and a second configuration after the deploying. The fastener limits relative movement between the first blood vessel and the second blood vessel when in the second configuration. An anastomosis between the first blood vessel and the second blood vessel is percutaneously produced.

The invention, together with additional features and advantages thereof, may best be understood by reference to the following description taken in conjunction with the accompanying illustrative drawings

BRIEF DESCRIPTION OF THE DRAWINGS

The invention, together with additional features and advantages thereof, may best be understood by reference to the following description taken in conjunction with the accompanying illustrative drawings

FIG. 4a is an end view of the arrangement shown in FIG. 4.

FIG. 7 is an isometric view showing the use of a catheter system to create an anastomosis between the two fixated blood vessels shown in FIGS. 6 and 6a.

FIG. 9b is an end view of the arrangement shown in FIG. 9.

FIG. 10b is an end view of the arrangement shown in FIG. 10.

DETAILED DESCRIPTION

Figure 1:
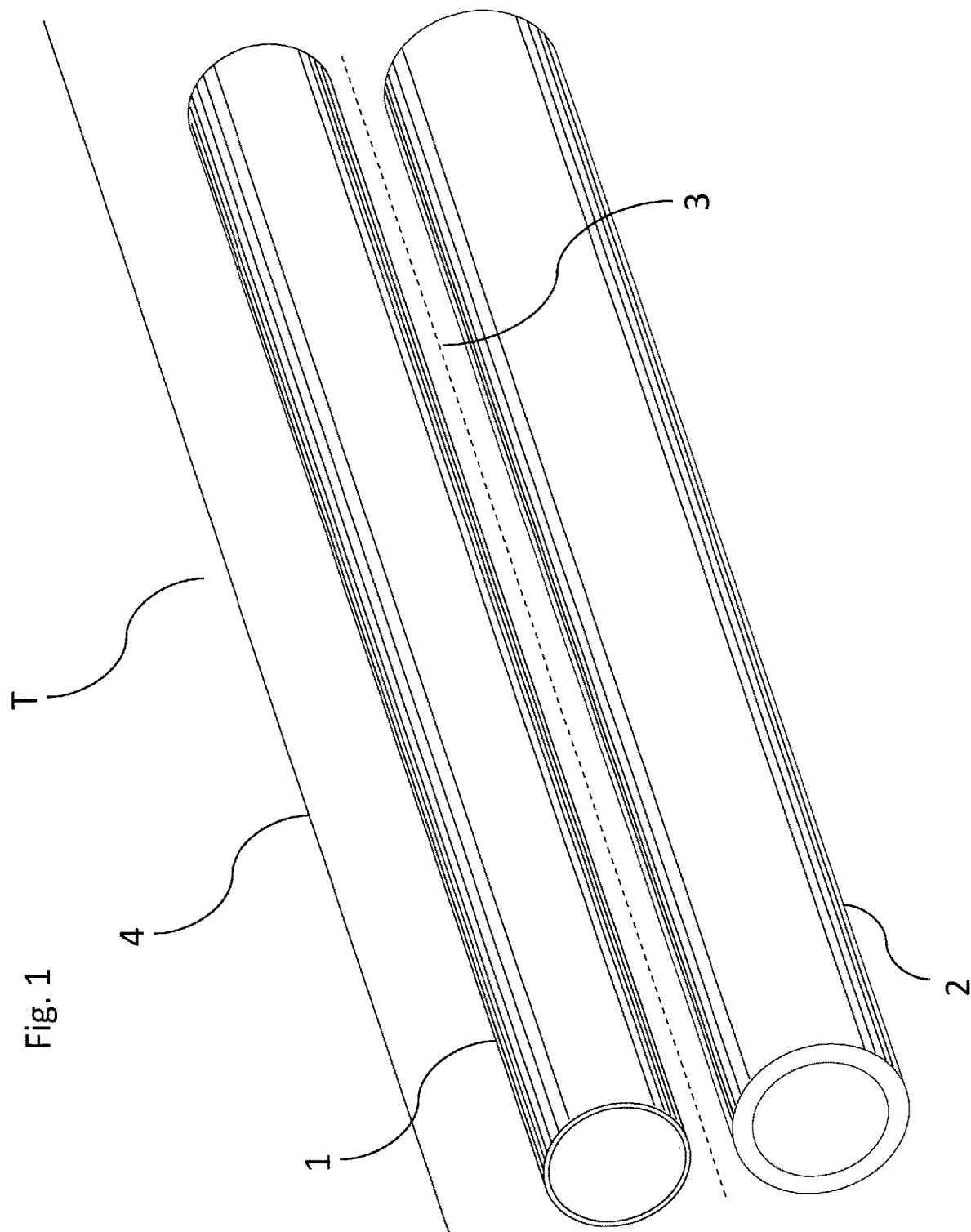
FIG. 1 is a simplified isometric illustration of two blood vessels lying adjacent to one another, separated by a layer of interstitial fascia.

The present invention involves a variety of devices, systems, and methods that are used to fixate a superficial vessel to an artery, prior to (or as a part of) creating an anastomosis. The primary mechanisms for the inventive systems and methods are based on mechanical fixation of the vessels through the use of fasteners, including sutures, slings, deformable members (including structures constructed from Nitinol® or other shape memory materials), or other structural means. The fasteners can be applied percutaneously either external to one or both of the blood vessels or internally within one or both of the blood vessels.

In some embodiments, a method of percutaneously creating a fistula includes inserting percutaneously a medical instrument to a target location having a first blood vessel and a second blood vessel. A fastener is then deployed via the medical instrument to the target location. The fastener is in a first configuration before the deploying and a second configuration after the deploying. The fastener limits relative movement between the first blood vessel and the second blood vessel when in the second configuration. An anastomosis between the first blood vessel and the second blood vessel is percutaneously produced.

In some embodiments, the deployment of the fastener can cause relative movement between the first blood vessel and the second blood vessel to place a side wall of the first blood vessel into engagement with a side wall of the second blood vessel. Similarly stated, in some embodiments, the deployment of the fastener can bring the first blood vessel and the second blood vessel together (either in direct contact or in sufficiently close proximity) and then limit relative movement of the vessels to facilitate the creation of the anastomosis.

In some embodiments, the fastener can be a flexible member (e.g., a suture, a sling, or other filament-like structure) that is deployed via the medical instrument into the desired position with respect to the first blood vessel and the second blood vessel. For example, in some embodiments, the flexible member can be deployed to surround at least a portion of each of the first blood vessel and the second blood vessel with a portion. In some embodiments, the method can optionally include applying a tension force to the flexible member to move the side wall of the first blood vessel into engagement with the side wall of the second blood vessel. In some embodiments, the method can optionally include fixating the first end of the flexible member to a first portion of skin outside of the target location and fixating a second end of the flexible member to a second portion of skin outside of the target location. The fixating can include at least one of forming a knot in the end, applying a fixation element to the end, or applying an adhesive to the end.

In some embodiments, the medical instrument can be separate from the device (e.g., a catheter assembly) used to create the fistula. For example, in some embodiments, the medical instrument can include an introducer, a needle, or both an introducer and a needle. In some embodiments, the method optionally includes advancing the needle within the target location to facilitate deployment of the flexible member. In some embodiments, the advancing the needle includes changing the curvature of the needle. In some embodiments, the inserting the medical instrument includes inserting a tip of the introducer. The needle is within a lumen of the introducer to maintain the needle in a first shape before the flexible member is deployed. The advancing the needle includes moving the needle out of the lumen of the introducer. The needle transitions to a second shape when moved out of the lumen. In some embodiments, the needle is constructed from a shape memory material. In some embodiments, the needle includes an alignment feature that is matingly received within the lumen of the introducer. The alignment feature maintains the needle in the desired orientation (i.e., ensures that the needle will bend in the desired direction when being advanced). Similarly stated, in some embodiments, the needle deforms about a predetermined bend axis when the needle is moved out of the lumen. The alignment feature of the needle is aligned with the predetermined bend axis.

In some embodiments, the fastener can be a deformable member that is introduced via the medical instrument and that deforms during deployment to limit movement of the vessels, move the vessels into the desired proximity with each other, and/or secure the vessels together. In some embodiments, the deformable member is maintained within a lumen of an introducer to maintain the deformable member in a first shape before it is deployed. The deploying can include advancing the deformable member out of the lumen and within the target location to surround a portion of each of the first blood vessel and the second blood vessel. The deformable member transitions to a second shape when moved out of the lumen.

In some embodiments, the fastener can be a deformable member that secures the first blood vessel to the second blood vessel from within the vessels. For example, in some embodiments, the fastener can be an implant clip that is deployed within the anastomosis. Thus, in some embodiments, the producing the anastomosis is performed before the implant clip is deployed and includes positioning at least one of a distal end of the medical instrument or a distal end of a catheter assembly to engage an inner surface of a side wall of the first blood vessel. A piercing member is then extended through the side wall of the first blood vessel and a side wall of the second blood vessel to produce a communicating aperture between the first blood vessel and the second blood vessel. The deploying then includes releasing the implant clip and moving a portion of the implant clip within the communicating aperture to secure the side wall of the first blood vessel to the side wall of the second blood vessel.

In some embodiments, the medical instrument for deploying the fastener can be the same device that is used to create the anastomosis. For example, in some embodiments, a catheter assembly can create the anastomosis (i.e., can produce the communicating aperture between the two vessels) and also deploy the fastener to secure the side wall of the first blood vessel to the side wall of the second blood vessel.

In some embodiments, a system for creating a percutaneous fistula includes a fastener, an introducer, and a catheter assembly. The fastener is configured to transition between a first configuration and a second configuration. The introducer is configured to facilitate percutaneous deployment of the fastener to a target location having a first blood vessel and a second blood vessel. The introducer defines a lumen within which at least a portion of the fastener is movably disposed. The introducer maintains the fastener in the first configuration when the portion of the fastener is within the lumen. The fastener is configured to transition to the second configuration when the fastener is deployed from the lumen to the target location. The fastener is configured to limit relative movement between the first blood vessel and the second blood vessel when in the second configuration.

In some embodiments, the fastener includes a deformable member having a first substantially linear shape when in its first configuration and a second curved shape when in its second configuration. The deformable member is configured to surround at least a portion of each of the first blood vessel and the second blood vessel when in its second configuration. In some embodiments, the deformable member can be a needle or a fixation device. In some embodiments, the deformable member is configured to deform about a predetermined bend axis when the deformable member is transitioned from its first configuration to its second configuration. The deformable member includes an alignment feature that is matingly received within the lumen of the introducer and that is aligned with the predetermined bend axis.

In some embodiments, the deformable member is a needle and the fastener includes a flexible member attached to the needle. The flexible member is configured to be advanced within the target location via the needle. The flexible member is configured to surround each surround at least a portion of each of the first blood vessel and the second blood vessel to secure the first blood vessel to the second blood vessel. The flexible member can be, for example, a suture or a sling.

In some embodiments, a system for creating a percutaneous fistula includes a catheter assembly, an implant clamp, and an actuator. The catheter assembly has a distal tip and a proximal base, with the distal tip being axially movable relative to the proximal base. The proximal base and the distal tip are configured to clamp a side wall of a first blood vessel and a side wall of the second blood vessel and produce an anastomosis between the first blood vessel and the second blood vessel. The implant clip is configured to be removably disposed within the catheter assembly. The implant clip is configured to be deployed within the anastomosis to secure the side wall of the first blood vessel to the side wall of the second blood vessel. The actuator is within the catheter assembly and is configured to deploy at least a portion of the implant clip to the anastomosis. The actuator is configured to release the implant clip from within the catheter assembly.

In some embodiments, the implant clip has a first portion and a second portion, and defines a clamp volume between the first portion and the second portion. The implant clip is configured to be disposed within the anastomosis to receive the side wall of the first blood vessel and the side wall of the second blood vessel within the clamp volume. In some embodiments, the implant clip is configured to deform from a first configuration to a second configuration to exert a clamp force on the side wall of the first blood vessel and the side wall of the second blood vessel.

In some embodiments, the actuator is configured to move the first portion of the implant clip away from the second portion of the implant clip to deploy the first portion of the implant clip to the anastomosis. In some embodiments, the actuator is configured to maintain the second portion of the implant clip within the catheter assembly when deploying the first portion of the implant clip. The actuator is further configured to release the second portion of the implant clip from within the catheter assembly after the first portion of the implant clip is deployed.

In some embodiments, the actuator includes an expandable element configured to move the first portion of the implant clip away from the second portion of the implant clip. In some embodiments, the expandable element is an inflatable member.

In some embodiments, a method of percutaneously creating a fistula includes advancing percutaneously a catheter assembly having an actuator, a distal tip, a proximal base and containing an implant clip in a distal direction within a target location until the distal tip of the catheter assembly passes through a first blood vessel and into a second blood vessel and the proximal base of the catheter assembly is within the first blood vessel. The distal tip is then moved in a proximal direction relative to the proximal base to clamp a side wall of the first blood vessel and a side wall of the second blood vessel. Energy is then conveyed to at least one of the proximal base or the distal tip to produce a communicating aperture between the first blood vessel and the second blood vessel. The actuator of the catheter assembly is manipulated to deform the implant clip to move a first portion of the implant clip outside of the catheter assembly while maintaining a second portion of the implant clip within the catheter assembly. The catheter assembly is then moved in a proximal direction to position the first portion of the implant clip in contact with a side wall of the second blood vessel. The actuator is manipulated to release the second portion of the implant clip from within the catheter assembly to place the second portion of the implant clip in contact with a side wall of the first blood vessel. The catheter assembly is then removed from the target location, leaving the implant clip within the target location.

In some embodiments, a system for creating a percutaneous fistula comprises a length of material capable of assuming both a curved and a straight configuration, an introducer configured to facilitate percutaneous entry of the length of material to a procedural site proximate to a pair of adjacent blood vessels, and a catheter device having opposed tissue clamping and cutting surfaces configured to clamp blood vessel wall tissue therebetween and to cut an anastomosis through the clamped blood vessel wall tissue. The length of material may comprise a curved needle which can be maintained in a straight configuration for percutaneous delivery to the procedural site. The introducer may comprise an instrument having clamping surfaces for holding and manipulating a proximal end of the curved needle. The introducer may comprise a primary needle having a lumen disposed therethrough. The curved needle and the primary needle lumen are keyed to ensure a proper orientation of the curved needle as it is advanced through the lumen. The length of material further comprises a length of suture attached to the curved needle, or a ring formed of one of a superelastic shape memory material and/or an absorbable elastic material, for example.

The catheter device may comprise a sliding distal tip and a proximal portion which are relatively movable, one of the opposed tissue clamping and cutting surfaces being disposed on the sliding distal tip and the other of the opposed tissue clamping and cutting surfaces being disposed on the proximal portion.

In some embodiments, a system for creating a percutaneous fistula, may comprise a catheter device having opposed tissue clamping and cutting surfaces configured to clamp blood vessel wall tissue therebetween and to cut an anastomosis through the clamped blood vessel wall tissue, an implant comprising deployable clamping members disposed on the catheter device, and a deploying member movable to separate the implant from the catheter device and to deploy the implant at a procedural site. The catheter device may comprise a sliding distal tip and a proximal portion which are relatively movable, with one of the opposed tissue clamping and cutting surfaces being disposed on the sliding distal tip and the other of the opposed tissue clamping and cutting surfaces being disposed on the proximal portion. The implant is disposed on the catheter device proximally of the sliding distal tip, and may comprise opposing arms which are movable relative to one another between a closed orientation and an open orientation. The deploying member comprises a rotational shaft movable distally to a position disposed between the opposing arms of the implant to move the opposing arms toward their open orientation and thereby separate the implant from the catheter device.

In some embodiments, a method for creating a percutaneous fistula includes steps of selecting an appropriate procedural site having each of a first blood vessel and a second blood vessel in close proximity to one another, securing the first and second blood vessels together using a mechanical fastener, and creating an anastomosis between the first and second blood vessels. The mechanical fastener comprises a curved needle and the securing step comprises inserting the curved needle percutaneously to the procedural site and positioning the curved need to extend around each of the two blood vessels and thereby secure them together. The curved needle is inserted through a lumen of a primary needle. The curved needle is further attached to a length of suture, and the curved needle is used to advance the length of suture so that the length of suture is wrapped about the first and second blood vessels, the method further comprising fixating an end of the length of suture to a portion of skin and tensioning the suture to approximate and hold the blood vessels in place.

Another step in the method described above is a step of fixating a second end of the length of suture to a second portion of skin. The mechanical fastener comprises a ring of material which is deformable to a straight configuration. The step of creating an anastomosis occurs before or after the step of securing the first and second blood vessels together using a mechanical fastener. The mechanical fastener may comprise an implant disposed on a catheter device adapted to perform the step of creating an anastomosis. The step of securing the first and second blood vessels together comprises deploying the implant from the catheter device. A further step comprises moving arms on the implant, after deployment from the catheter, from an open position to a closed position to clamp blood vessel walls at the procedural site, adjacent to the newly formed anastomosis.

The term "about" when used in connection with a referenced numeric indication means the referenced numeric indication plus or minus up to 10 percent of that referenced numeric indication. For example, "about 100" means from 90 to 110.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls or structural components. Such a set of walls or structural components can include, for example, multiple portions that are either continuous or discontinuous from each other. A set of walls or structural components can also be fabricated from multiple items that are produced separately and are later joined together (e.g., via a weld, an adhesive, or any suitable method).

As used herein, the term "flexible" or "flexibility" relates to an object's resistance to deflection, deformation, and/or displacement produced by an applied force, and is generally understood to be the opposite of the object's "stiffness." For example, a securing member (e.g., a suture, sling, deformable ring, or clip) with greater stiffness is more resistant to deflection, deformation and/or displacement when exposed to a force than is securing member having a lower stiffness. Similarly stated, a securing member having a higher stiffness can be characterized as being more rigid than a securing member having a lower stiffness. Flexibility can be characterized in terms of the amount of force applied to the object and the resulting distance through which a first portion of the object deflects, deforms, and/or displaces with respect to a second portion of the object.

Stiffness (and therefore, flexibility) is an extensive property of the object being described, and thus is dependent upon the material from which the object is formed as well as certain physical characteristics of the object (e.g., cross-sectional shape, thickness, boundary conditions, etc.). For example, the stiffness of an object can be increased or decreased by selectively including in the object a material having a desired modulus of elasticity, flexural modulus and/or hardness. Moreover, the stiffness (and therefore flexibility) of an object constructed from a polymer can be influenced, for example, by the chemical constituents and/or arrangement of the monomers within the polymer. For example, the stiffness of an object can be reduced by decreasing a chain length and/or the number of branches within the polymer. The stiffness of an object can also be reduced by including plasticizers within the polymer, which produces gaps between the polymer chains.

As used in this specification, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

FIG. 1 is a simplified illustration of a target location T for the creation of a fistula. The target location includes a first blood vessel 1, typically a vein, and a second blood vessel 2, typically an artery, separated by a layer of interstitial fascia 3. The blood vessels 1 and 2 are disposed superficially beneath a skin layer 4. In particular, oftentimes, the vein 1 is superficial relative to the surface of the skin 4, and the artery 2 is deeper, with the interstitial fascia layer separating the two vessels. Since the interstitial fascia layer 3 creates a slip plane between the vessels 1, 2 and allows the vessels to move independently between each other, it can be desirable to fixate the vessels prior to create an anastomosis between them.

Figure 2:
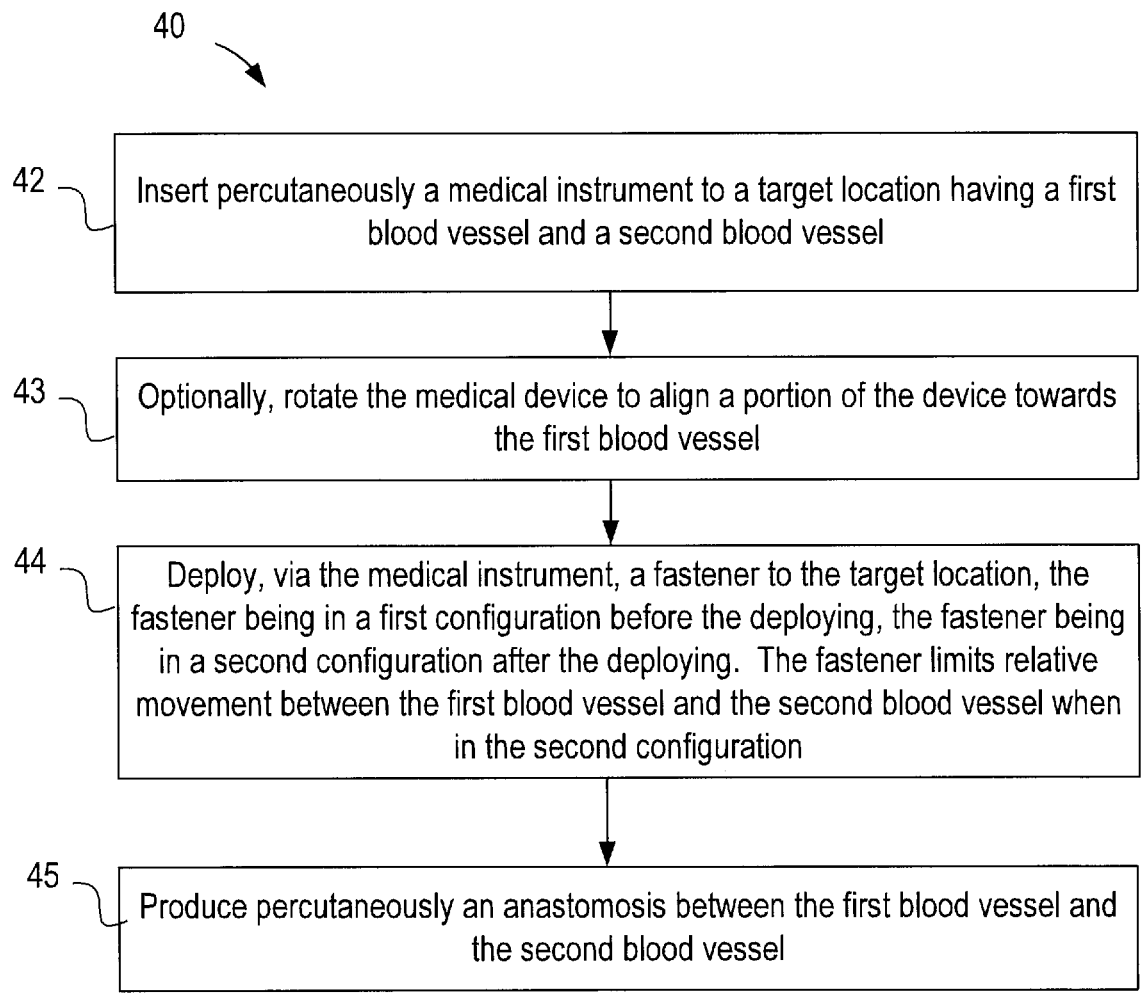
FIG. 2 is a flow chart of a method of percutaneously creating a fistula according an embodiment.
Figure 3:
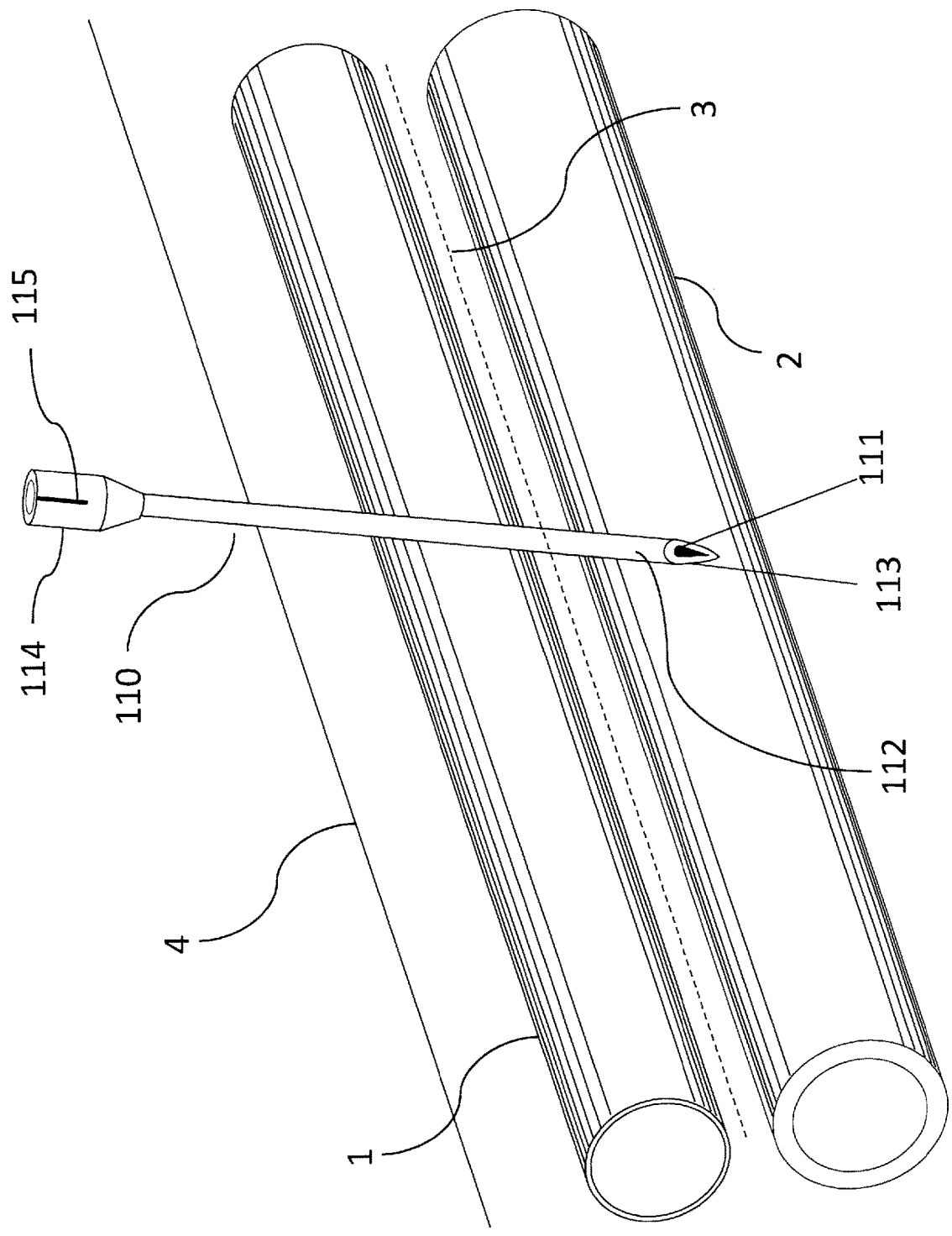
FIG. 3 is a view similar to FIG. 1, wherein an introducer has been percutaneously inserted alongside one of the blood vessels.
Figure 4:
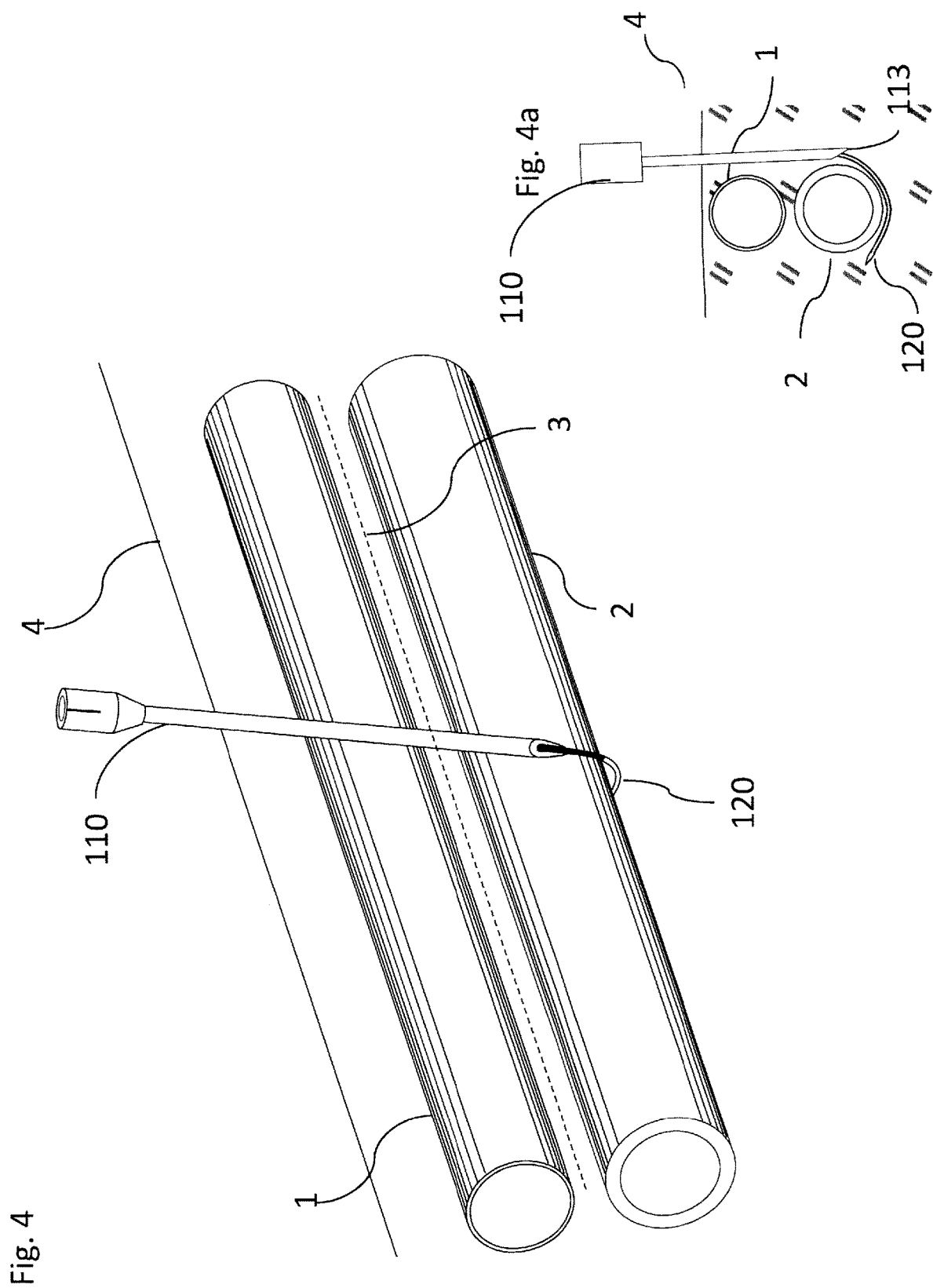
FIG. 4 is a view similar to FIGS. 1 and 3, illustrating the advancement of a curved needle through a lumen in the previously positioned introducer shown in FIG. 3.
Figure 5:
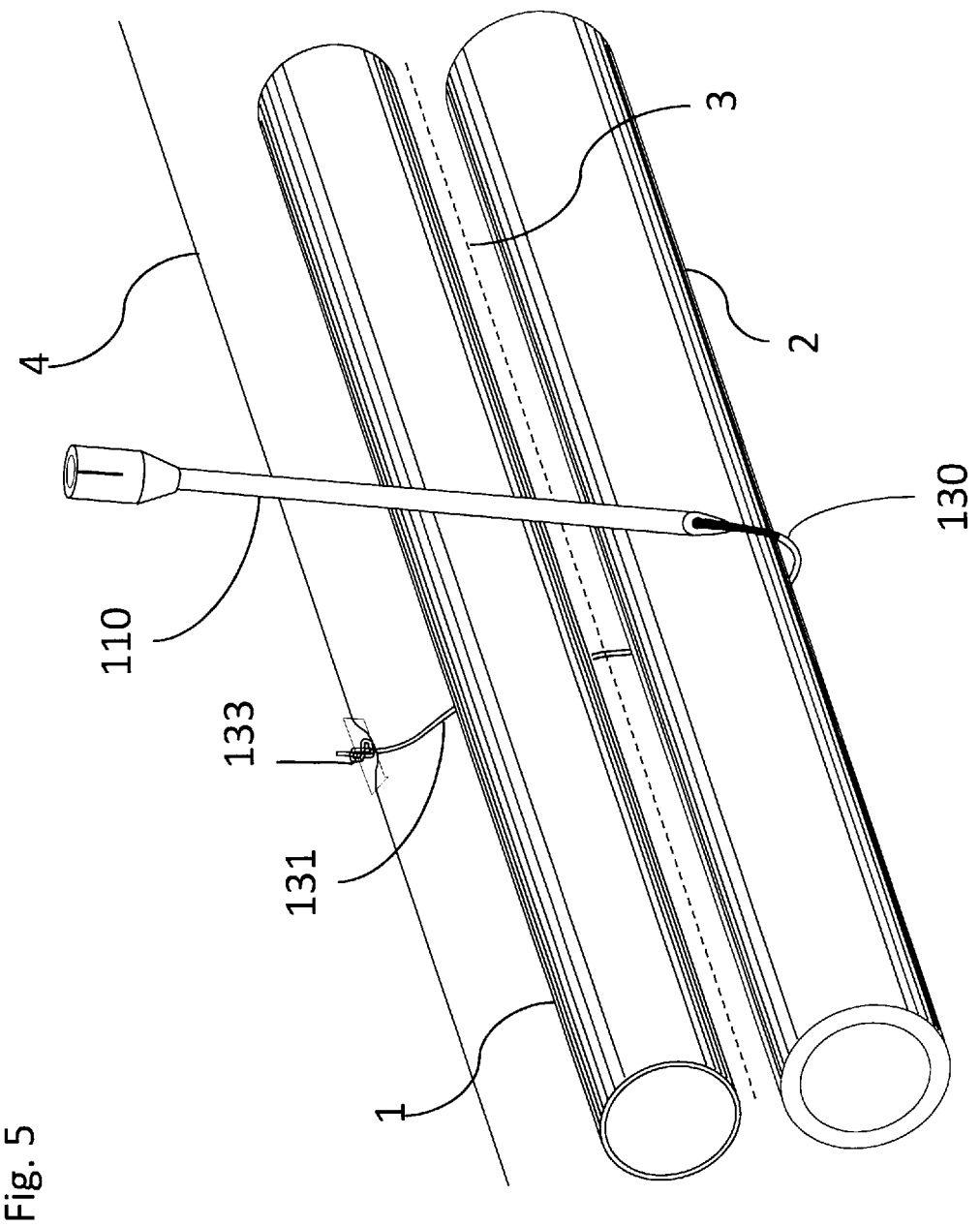
FIG. 5 is a view similar to FIGS. 1, 3-4, illustrating a flexible member being applied and fixated to the skin on one side to bring the blood vessels into proximity.

FIG. 2 is a flow chart of a method 40 of percutaneously creating a fistula according to an embodiment. The method 40 is described in connection with schematic illustrations of FIGS. 3-8, which depict the creation of a fistula at the target location T. Although the method 40 is described as being performed with the medical instrument (or introducer) 110 and catheter assembly 160, in other embodiments, the method 40 is not limited to the specific instruments and devices shown in FIGS. 3-8, but can be performed using any suitable instruments and devices of the types shown and described herein. For example, although FIGS. 3-5 show the use of the introducer 110 to create a fistula, in other embodiments, the method 40 can be performed using forceps (e.g., the forceps 226 shown in FIG. 11).

The method 40 includes inserting percutaneously a medical instrument to a target location having a first blood vessel and a second blood vessel, at 42. The medical instrument can be any suitable medical instrument of the types shown and described herein. For example, referring to FIGS. 3-5, the medical instrument can include an introducer 110 and/or a needle 120. As shown, the introducer 110 includes a distal tip 112 and a proximal hub 114 and defines a lumen 111 therethrough. The distal tip 112 includes a beveled surface 113 that can pierce, dilate and/or displace bodily tissue during the insertion. Moreover, the beveled surface 113 can guide the exit path of the needle 120 (see FIGS. 4 and 4a) to ensure that the needle 120 is properly positioned during its deployment. In some embodiments, the proximal hub 114 can include one or more alignment marks (or indicators) 115.

Referring again to FIG. 3, the introducer 110 is positioned alongside the artery 2. The introducer 110 can be positioned using ultrasound guidance or other suitable visualization techniques such that it is positioned close to the artery 2 and at the desired depth relative to the artery 2, as shown. In some embodiments, the distal tip 112 can include a radio-opaque marker that can be used to gauge the depth of insertion. In other embodiments, the introducer 110 can include graduated markings to provide a depth indicator. The introducer 110 may also have other features to improve its echogenicity, such as a roughened surface or coating. Moreover, the introducer 110 is oriented such that the beveled surface 113 on the distal end 112 faces the artery 2. In order to facilitate proper orientation of the introducer 110, there are visual features on the hub or markings on the shaft and/or hub (e.g., the alignment marks 115) for guiding the practitioner. These features may comprise molded features on the needle hub or ink markings on the shaft and/or hub. Accordingly, in some embodiments, the method optionally includes rotating the introducer to align the beveled surface towards the first blood vessel, at 43.

Referring to FIG. 2, the method includes deploying, via the medical instrument, a fastener to the target location, at 44. The fastener is in a first configuration before the deploying and in a second configuration after the deploying. The fastener limits relative movement between the first blood vessel and the second blood vessel when in the second configuration. As described above, in some embodiments the medical instrument can be (or include) a needle that is used to deploy the fastener. As shown in FIG. 4, in some embodiments, the medical instrument includes both the introducer 110 and the needle 120. After the introducer 110 is positioned, the curved needle 120 is advanced through the inner lumen 111 (FIG. 3) of the introducer 110. In some embodiments, the curved needle 120 is constructed from an elastic shape memory material, such as the nickel-titanium alloy commonly identified by the trade name Nitinol®, so that it can pass through the straight introducer 110. Thus, the advancement of the needle results in changing the curvature of the needle 120. In other embodiments, the curved needle 120 can be constructed from an elastic material that has sufficient rigidity to be maintained in a linear configuration while within the lumen 111 and revert to a curved configuration after being deployed. In some embodiments, the needle 120 is configured to deform or bend about a predetermined bend axis when the needle 120 is moved out of the lumen 111. In this manner, the needle 120 can be directional and/or can also have a predetermined radius of curvature when the second (or deployed configuration). Thus, in some embodiments, the curved needle 120 has one or more alignment features, such as an oblong shape or other means, so that it keys into the inner lumen 111 of the introducer 110 to ensure that it curves in the correct orientation around the artery 2 as it exists the introducer 110. The curved needle 120 is advanced using suitable imaging guidance, such as ultrasound guidance, until it exits the skin 4 on the opposite side of the vessels 1 and 2 (FIG. 5).

Figure 6A:
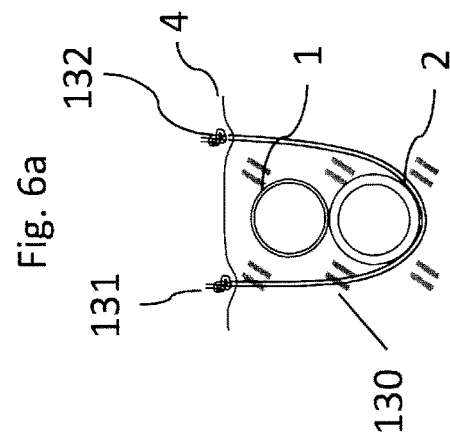
FIG. 6a is an end view of the arrangement shown in FIG. 6.
Figure 6:
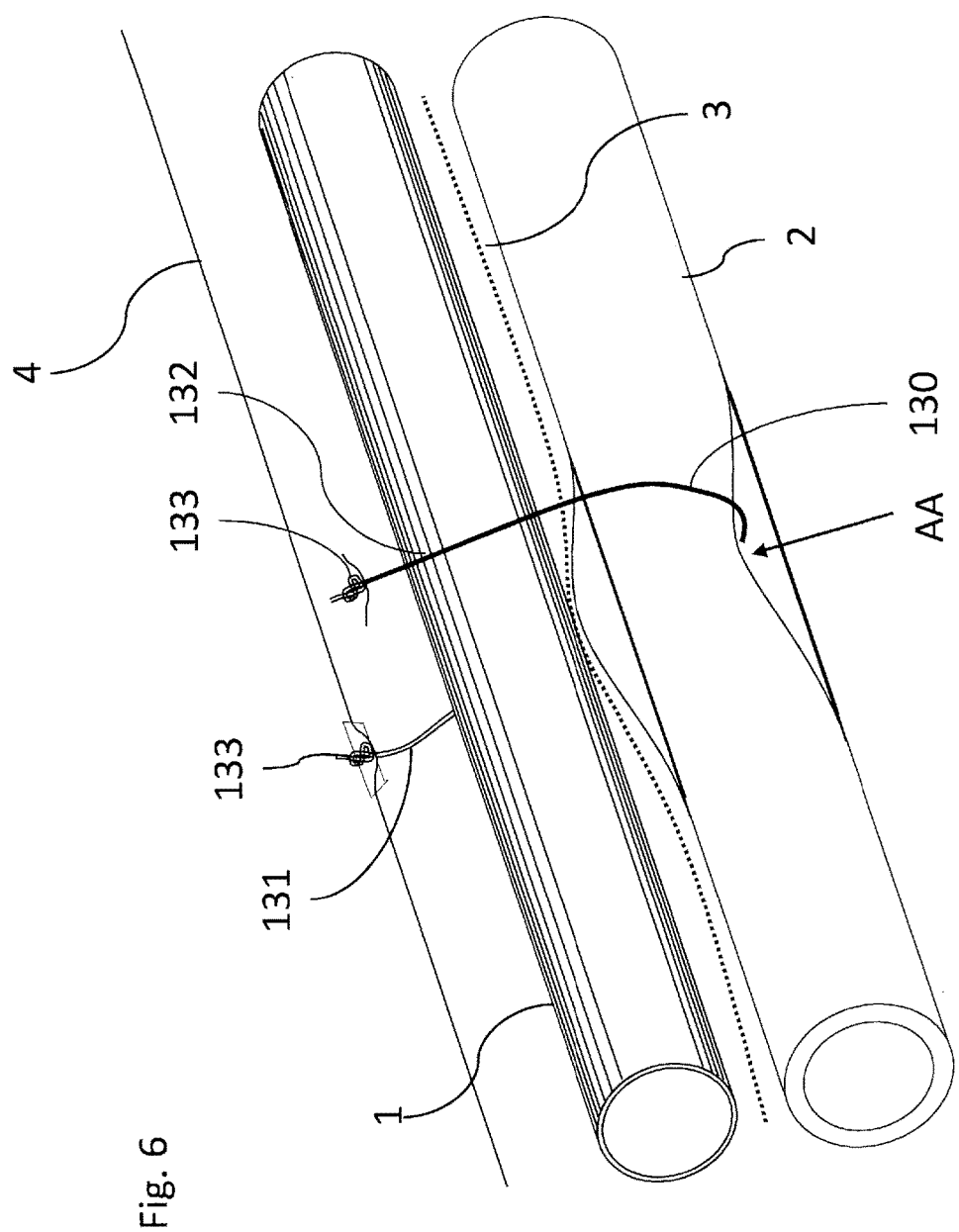
FIG. 6 is a view similar to FIGS. 3-5, wherein the flexible member has been fixated to the skin on each side of the blood vessels and the needle has been withdrawn.

In some embodiments, the fastener can be a flexible member, such as a suture, a sling, or a filament-like structure. For example, referring to FIG. 5, in some embodiments, a suture 130 is coupled to (or included as a part of) the end of the needle 120. Thus, as the needle is advanced, the suture 130 (and the needle 120) surround at least a portion of each of the first blood vessel 1 and the second blood vessel 2. Similarly stated, the deploying of the flexible member can include wrapping (or partially wrapping) the flexible member about one or both of the vessels. The curved needle 120 is cut off (or otherwise removed) from the suture 130 once it has been drawn through the skin surface 4. In some embodiments, the method includes securing (or fixating) a first end 131 of the suture 130 to a first portion of skin 4 outside of the target location. The method can also optionally include securing (or fixating) a second end 132 of the suture 130 to a second portion of skin 4 outside of the target location. The ends of the suture (or any of the flexible members described herein) can be secured to the skin by any suitable mechanism. For example, as shown in FIGS. 6 and 6a, the ends of the suture can be secured using a knot 133. In other embodiments, other suitable fixation approaches can be used, such as adhesive or a mechanical fastener.

As described above, after the fastener is deployed (i.e., when in its second configuration), the fastener limits relative movement between the first blood vessel and the second blood vessel. In this manner, the vessels can be in a fixed position for the creation of the anastomosis. In other embodiments, the deploying the fastener can also include moving the first blood vessel and/or the second blood vessel. In this manner, the two vessels can be moved into sufficiently close proximity with each other to facilitate percutaneously producing the fistula. In some embodiments, the first blood vessel and the second blood vessel can be moved into contact with each other (either directly or through a nominal layer of interstitial tissue). For example, referring to FIGS. 6 and 6a, in some embodiments, after the first end 131 of the suture 130 is fixed to the skin 4, tension is applied to the suture 130. This tension and fixation brings the artery 2 and vein 1 together, as shown by the arrow AA in FIG. 6. This creates a loop of suture 130, under tension, which cradles both the vein 1 and artery 2 together, as shown in FIGS. 6 and 6a. Typically, the suture 130 is left in place for a suitable period of time, such as 1-2 weeks, so that the anastomosis has time to heal and stabilize. The suture material 130 may be comprised of a dissolving type of material, such as polyglactin or polyglycolic acid, or, alternatively, a non-dissolving material which later is removed.

Figure 7:
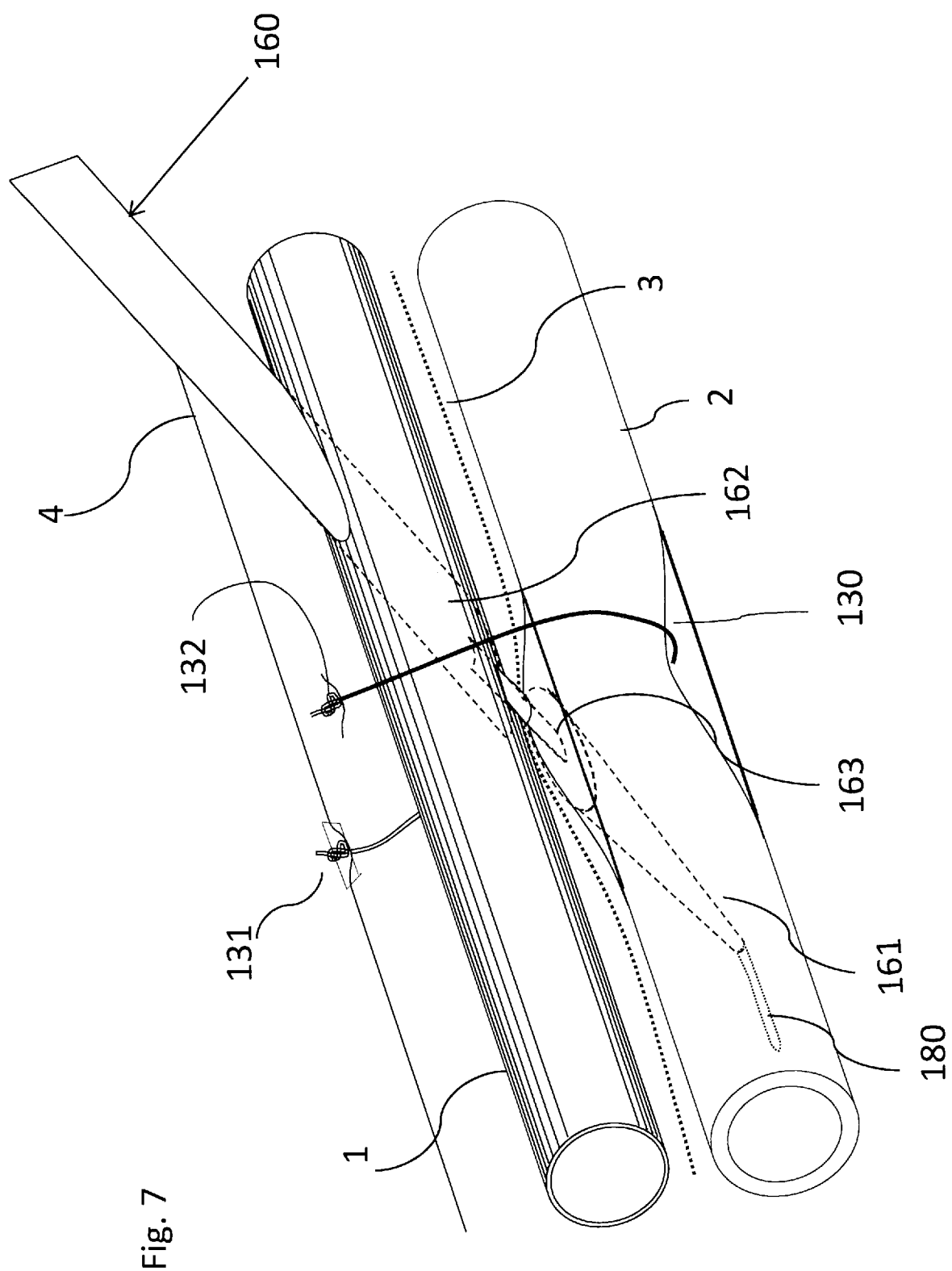
Figure 8:
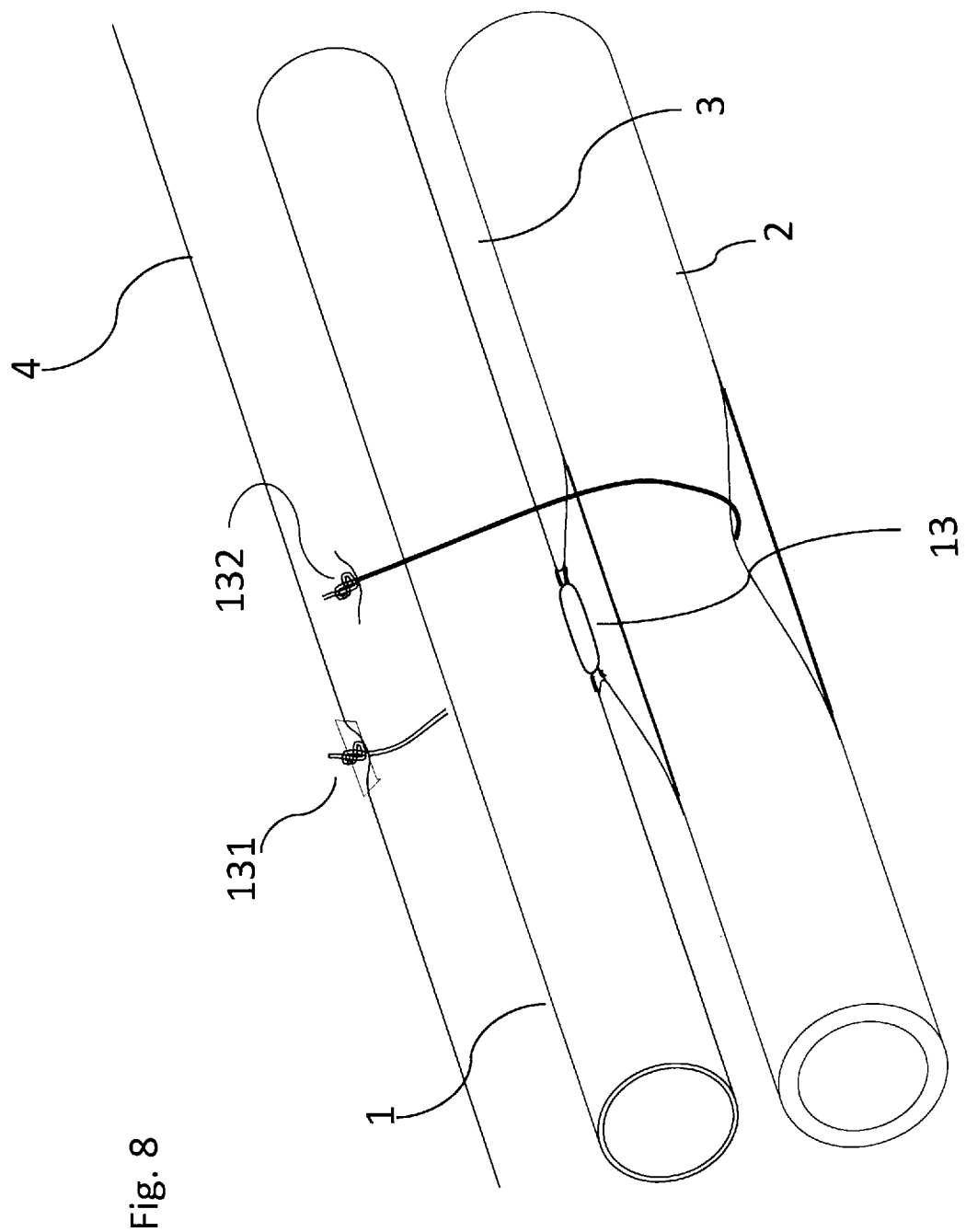
FIG. 8 is an isometric view showing the fixated blood vessels which have been joined by the created anastomosis, after the catheter system has been removed.

Referring again to FIG. 2, the method includes producing percutaneously an anastomosis between the first blood vessel and the second blood vessel, at 45. The anastomosis can be produced by any suitable instrument, such as any of the catheter assemblies disclosed, for example, in Applicant's prior U.S. Pat. Nos. 9,138,230; 9,439,710; 9,439,728; 9,452,015; and 9,474,562, all of which are herein expressly incorporated by reference, in their entirety. As one example, FIGS. 7 and 8 illustrate, generally, one method for creating an anastomosis between the vessels 1, 2 which have been secured together using flexible member in a manner similar to that described above. In particular, the anastomosis is produced using a catheter assembly 160 having a central lumen that is capable of tracking over a guidewire 180 from vessel 1, typically a vein, into the adjacent vessel 2, typically an artery. The catheter assembly 160 has a distal tip 161, a proximal base 162, and a sliding element 163 about which the distal tip 161 can move relative to the proximal base 162. The distal and proximal elements 161, 162, respectively, have two parallel opposed surfaces, and are separated by the sliding element 163. The opposed parallel surfaces are typically disposed at a shallow angle relative to the luminal axis, as shown in FIG. 7, to increase the surface area between them. The angle of disposition is typically between 15 and 45 degrees, with a preferred angle of about 23 degrees. The catheter assembly is positioned so that the sliding distal tip 161 is positioned in vessel 2 and a proximal portion 162 is positioned in vessel 1. With the distal element 161 in the artery 2, the distal element 161 is retracted relative to the proximal element 162. As the elements 161, 162 slide toward one another, the vessel walls are captured between the opposed parallel surfaces of the elements. Energy is applied to the catheter elements to ablate the tissue captured between the elements and to seal the vessel walls together along the circumference by modifying the collagen matrix in the surrounding tissues. The ablated tissue between the two vessels creates an anastomosis between them, and the catheter is removed, leaving the completed anastomosis 13 (FIG. 8). The methods and inventions described herein may be utilized either before or after placement and activation of the catheter, as described in more detail herein.

Figure 9:
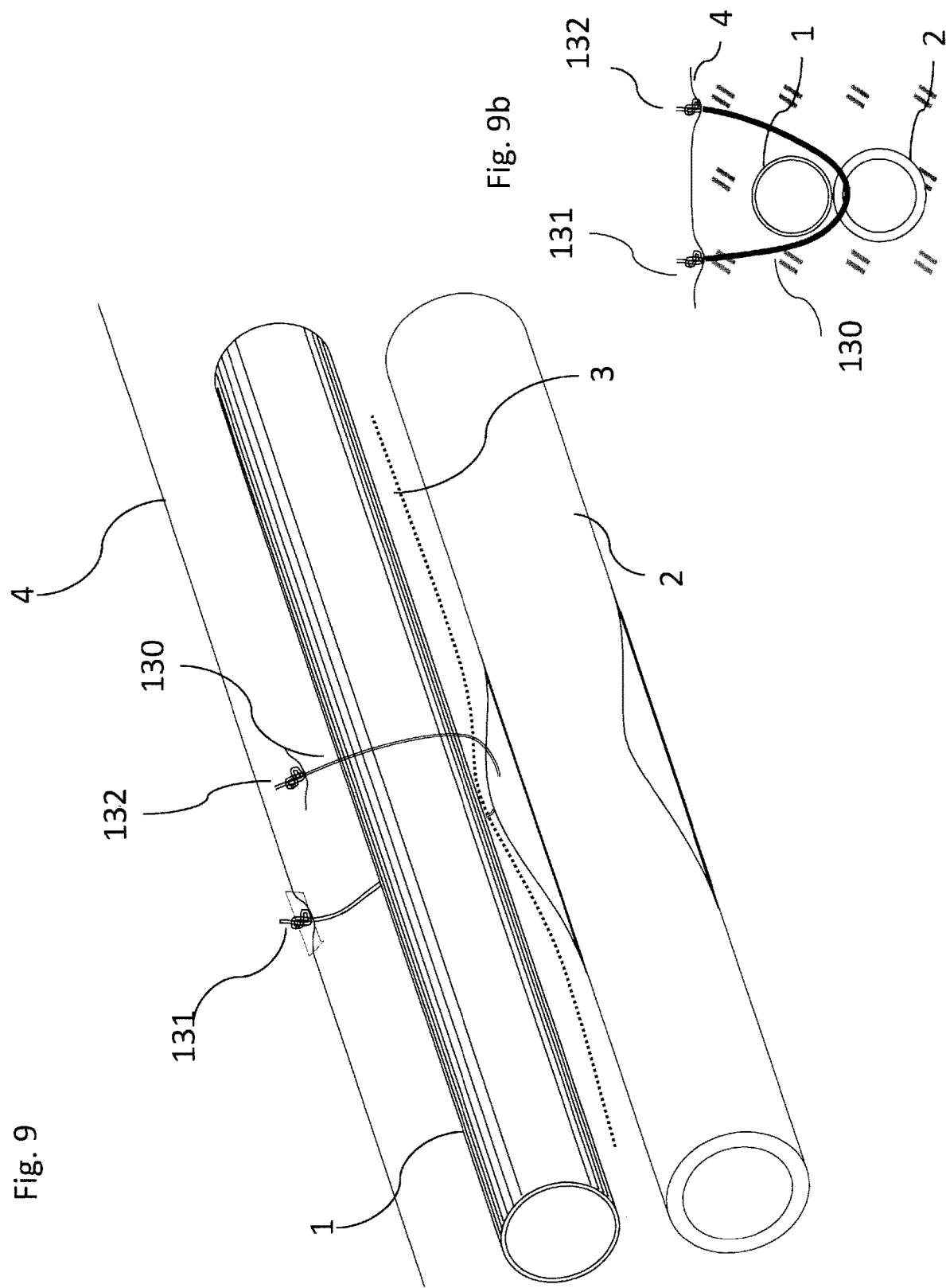
FIG. 9 is a view similar to FIGS. 3-6a showing an alternative method for securing the blood vessels together.
Figure 10:
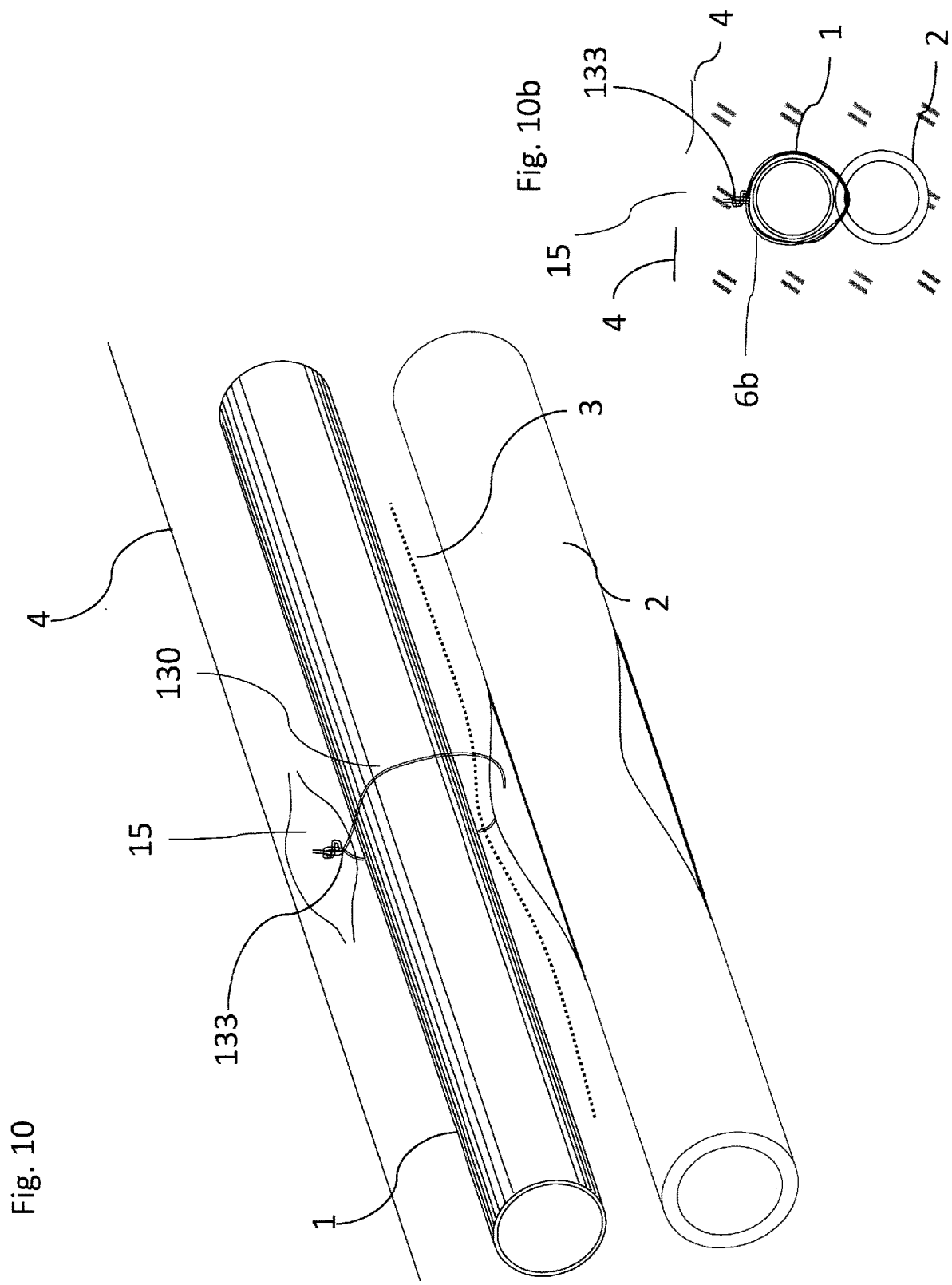
FIG. 10 is a view similar to FIGS. 3-6a showing another alternative method for securing the blood vessels together.

There are several alternative devices and methods which may be used to accomplish similar results to the embodiment and method discussed above, within the parameters of the present invention. For example, as shown in FIGS. 9 and 9b, instead of suturing below the artery 2 as shown in FIGS. 4-8, in other embodiments, the suture 130 (or any other suitable flexible member) may be placed through the top, or superior wall, of the artery 2. This approach can be helpful in preventing the tension applied by the suture from narrowing or collapsing the arterial lumen. In this circumstance, the anastomotic catheter (see FIG. 7) is positioned either proximally of or distally to the suture 130.

FIG. 7 illustrates yet another variation, wherein, instead of attaching the suture 130 to the skin 4 via two separate fixation points, the suture is placed around the vein 1 through a small skin incision 15. Through the incision 15, the two free ends of the suture 130 are joined by means of a knot 133 or other suitable fastening approach. This approach may be indicated when the vessels 1, 2 are too deep and not enough tension can be applied to the suture to bring the vessels into close approximation using the above-described approaches.

Figure 11:
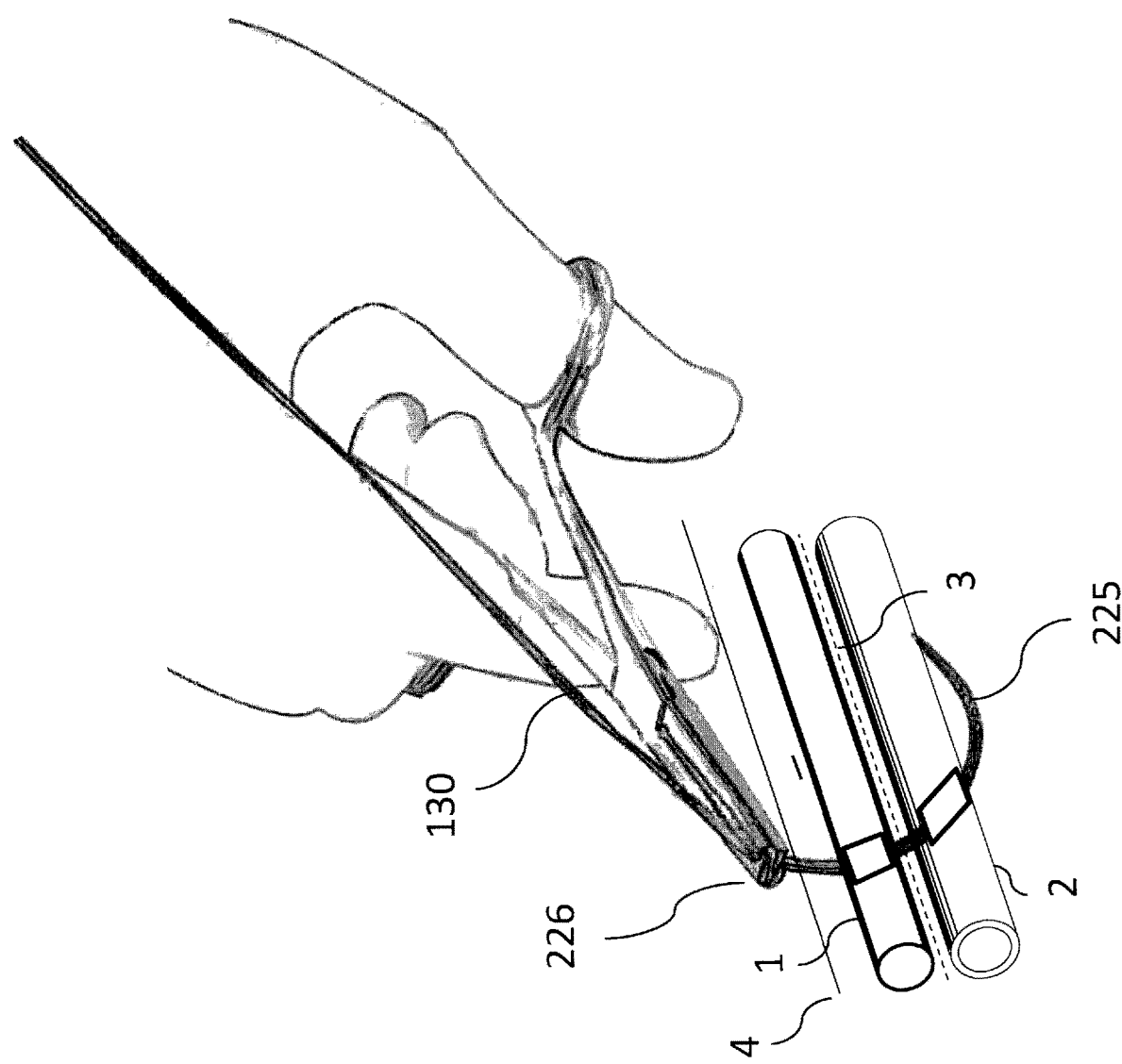
FIG. 11 is an isometric view showing yet another system and method for fixating blood vessels that are superficial.

Although the medical instrument is shown in FIGS. 3-5 as including an introducer 110 and a needle 120, in other embodiments, a medical instrument used to deploy a fastener can be any suitable medical instrument. For example, in some embodiments, the method 40 need not be performed using an introducer. For example, in some instances, if the vessels 1, 2 are sufficiently superficial, as shown in FIG. 11, the introducer 110 may not be necessary, and a standard curved suturing needle 225 may be used. In such a method, the practitioner may directly insert the distal end of the needle 225 through the skin 4 and manipulate the needle 225 to the illustrated position around the vessels 1, 2 using the distal end of a suitable instrument 226 such as forceps for clamping and manipulating the proximal end of the needle. The suture 130 can then be secured in place while the anastomosis is created and established, as desired.

Figure 12:
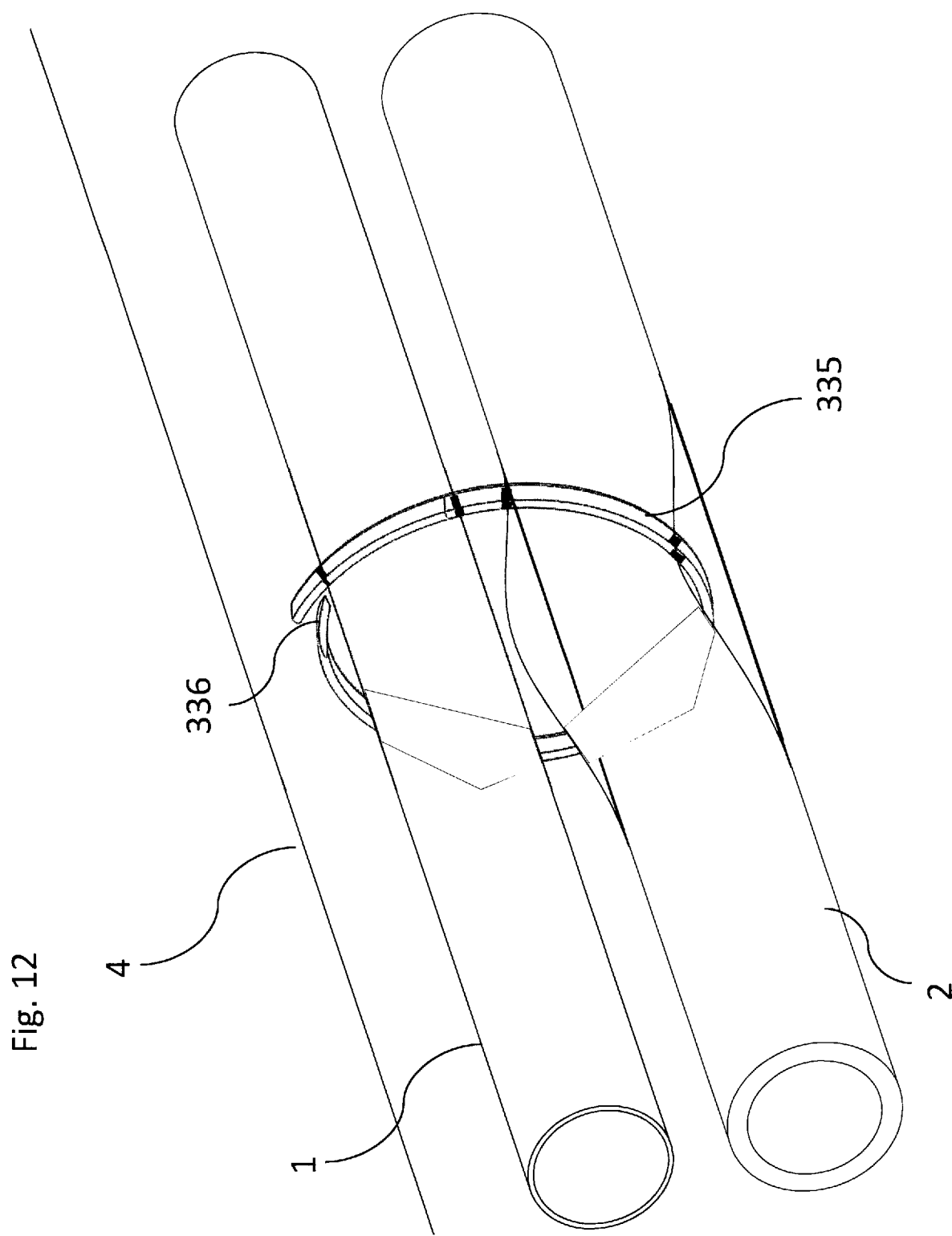
FIG. 12 is a view showing still another system and method for fixating the blood vessels.

Although the fastener is shown and described above as being a flexible member, such as a suture or a sling, in other embodiments, the fastener can have any suitable rigidity. For example, in some embodiments, the fastener can have sufficient rigidity to maintain its shape, thereby exerting a force (or limiting relative movement between the first vessel and the second vessel) without being separately secured (or fixated) to the skin. Said another way, in some embodiments, the fastener can be a ring, clip, or clamp that need not be tied together. For example, FIG. 12 shows a fastener 335 according to an embodiment. The fastener 335 a ring that can be used to achieve fixation of the vessels 1, 2. Instead of using suture to secure the vessels, the circular ring 335 may be advanced through the introducer 110 or any other suitable medical instrument (not shown in FIG. 12) in accordance with the methods described herein. In some embodiments, the ring 335 is formed of a superelastic shape memory material, such as Nitinol®, so that as it is advanced out of the medical instrument (e.g., the introducer) it assumes its deployed circular configuration in order to curve around the vessels. In this manner, the fastener 335 is a deformable member that is maintained in a first shape (e.g., linear) before being deployed, and transitions to a second shape (e.g., curved) when being deployed. The ring 11 may also be made of an absorbable material, such as polylactic acid. In some embodiments, the leading edge 336 of the ring is beveled so that it is able to dissect the tissue as it is advanced. Although a sharp lancet point may be used, it may be preferable that it have a slightly rounded edge to prevent it from puncturing one or both of the vessels. In some embodiments, the fastener 335 has alignment features that help to maintain the proper orientation of the fastener 335 inside the medical instrument (e.g., the introducer 110) in order to ensure that the ring curves in the correct direction.

Figures 13, 13A, 13B:
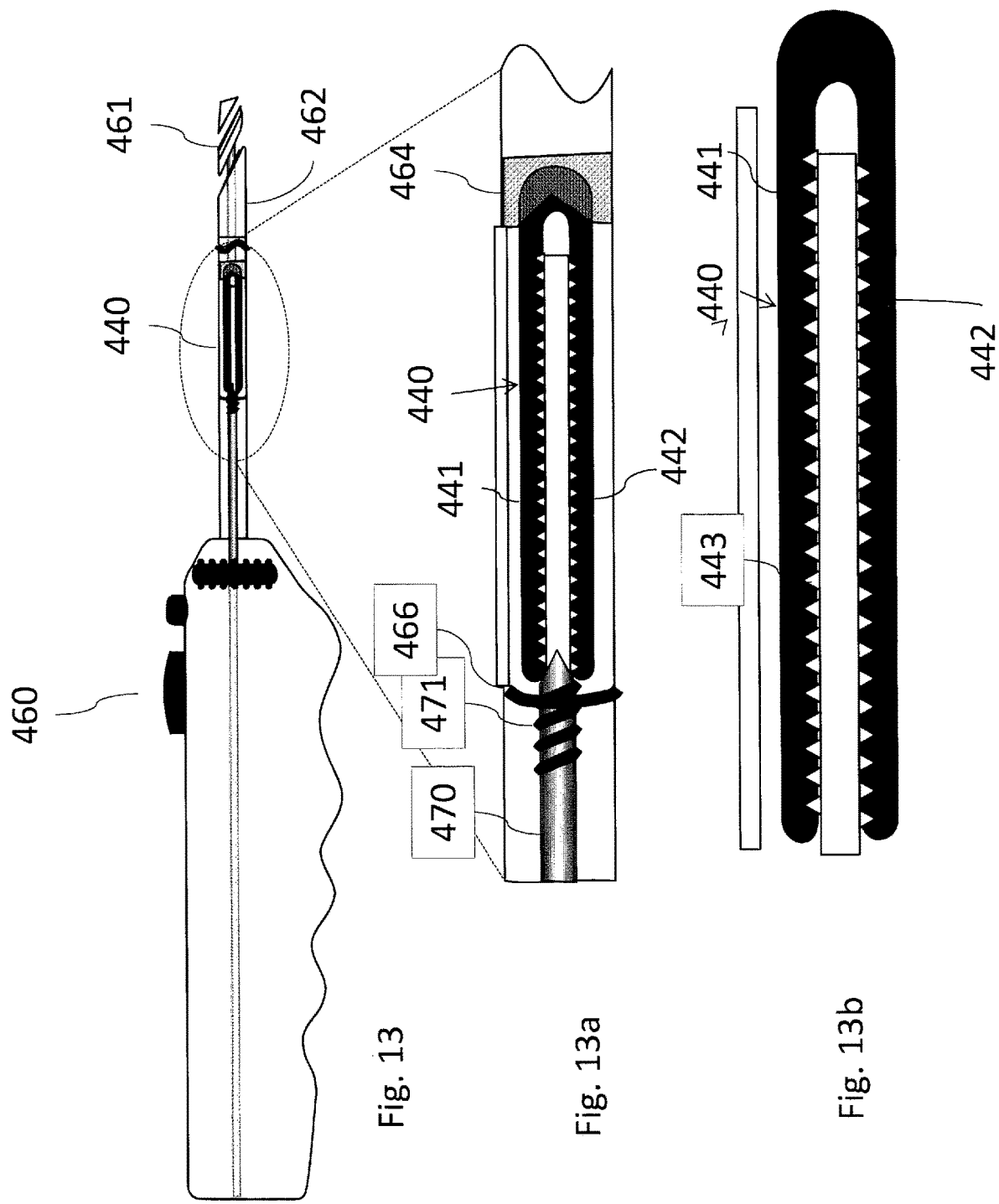
FIG. 13 is a schematic plan view of an alternative system for fixating two blood vessels together after creation of an anastomosis.
FIG. 13a is an enlarged plan view of a portion of a distal end of the device shown in FIG. 13.
FIG. 13b is a plan view of a clip dispensable from the device shown in FIGS. 13 and 13a for securing the blood vessels together after creation of an anastomosis.

Although the method 40 described above includes a medical device (e.g., the introducer 110, the needle 120, and/or the needle 225) to deploy a fastener that is separate from the catheter assembly (e.g., the catheter assembly 160) that forms the communicating aperture or anastomosis between the two vessels, in other embodiments, a single device can be used to create the anastomosis and deploy a fastener. Moreover, although the method 40 described above includes placing the fastener outside of the vessels, in other embodiments, a method can include securing the vessels by placing a fastener in contact with the interior side walls of the vessels. For example, FIGS. 13, 13a and 13b show a deliver catheter 460 and an implant clip 440 that allows the vessels to be fixated internally after the anastomosis is created. The catheter assembly 460 is capable of creating an anastomosis similar to the catheter discussed in connection with the previously disclosed embodiments, and also deploying an implant clip 440 that is designed to clip the walls of the vessels together internally. Although both of these functions are described in connection with a single catheter 460, in other embodiments, two separate catheters may be used in order to achieve the same functionality.

Figure 26:
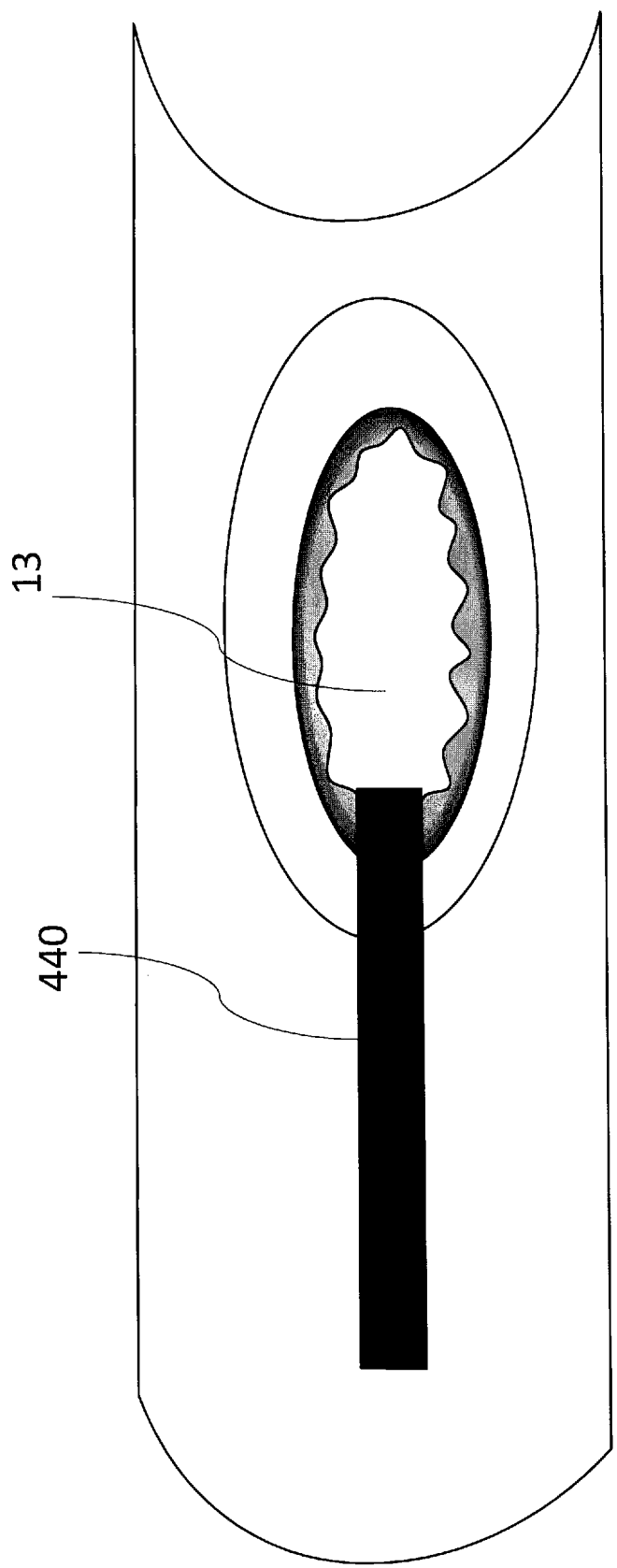
FIG. 26 is a schematic view illustrating the anastomosis with the mechanical fixation device in place.

The catheter assembly 460 is constructed in a manner similar to that of the catheter assembly 160 previously described herein, having a proximal portion 462 into which the clip 440 is disposed, and a sliding distal tip 461. As described above, the distal and proximal elements have two parallel opposed surfaces between which the vessel walls can be clamped. At least one of the parallel surfaces includes a heater or other energy transmitting element. Thus, when the vessel walls are captured between the opposed parallel surfaces of the elements, energy is applied to at least one of the distal tip 461 or proximal base 462 to ablate the tissue captured between the elements and to seal the vessel walls together along the circumference by modifying the collagen matrix in the surrounding tissues. The ablated tissue between the two vessels creates an anastomosis between them, and the catheter is removed, leaving the completed anastomosis 13 (FIG. 26). In addition to including the parallel surface (and/or energy transmitting element), the proximal portion 462 includes a bulkhead 464 within which the implant clip 440 can be removably disposed. The bulkhead 464 defines a volume within the implant clip 440 is maintained and define a side opening (or slot) 465 through which the implant clip 440 can be deployed. The bulkhead 464 can also maintain longitudinal and rotational orientation of the implant clip 440 prior to release of the implant clip 440 from the catheter assembly 460.

The catheter assembly 460 is coupled to (or includes) an actuator 470. The actuator includes a deployment element 471. As described herein, the actuator 470 is configured to deploy at least a portion of the implant clip 440 to the anastomosis 13 and also release the implant clip 440 from within the catheter assembly.

Figure 24:
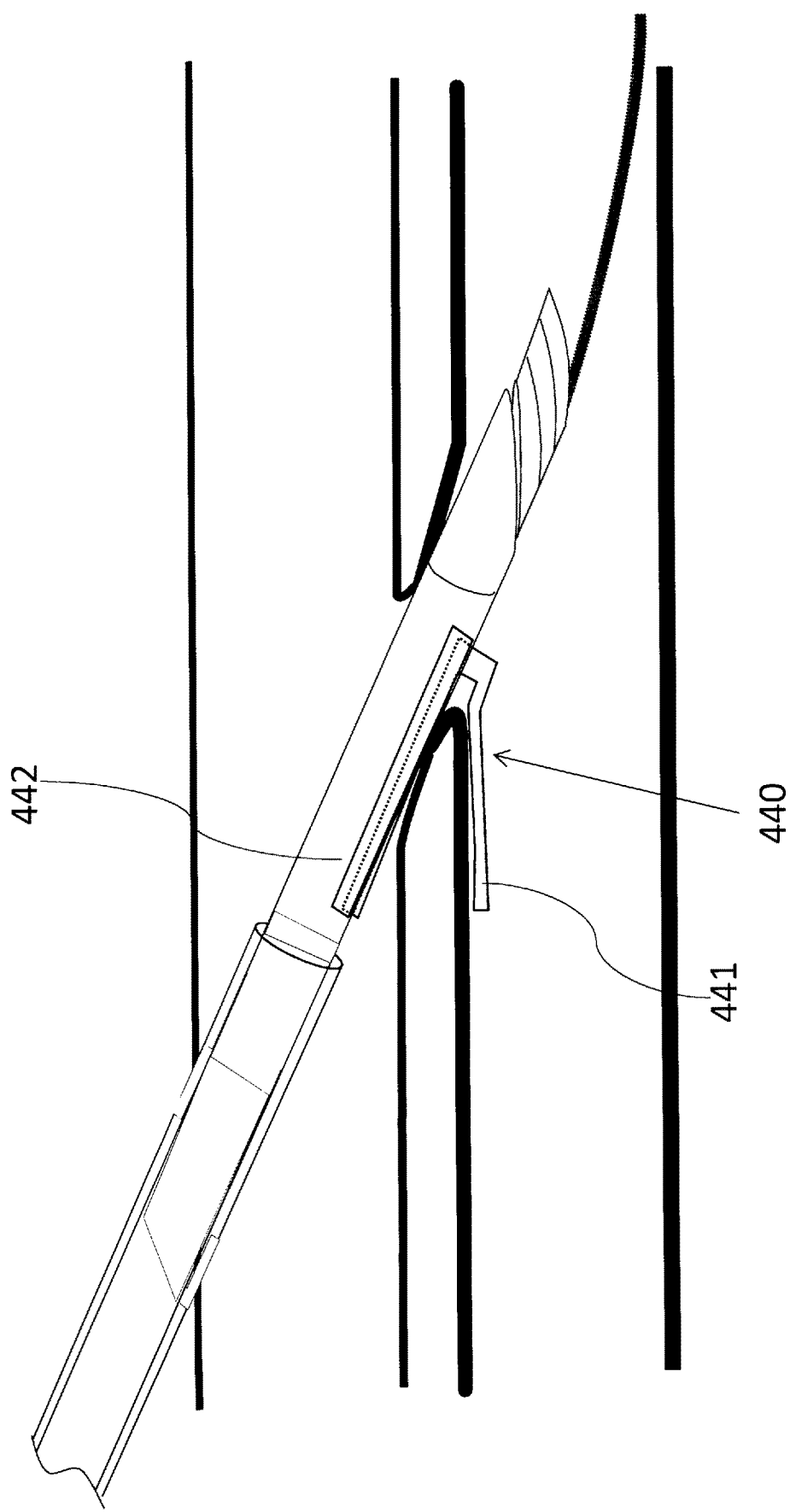
FIG. 24 is a view similar to FIGS. 18-23 wherein the mechanical fixation device is fully engaged on one end of the anastomosis.
Figure 25:
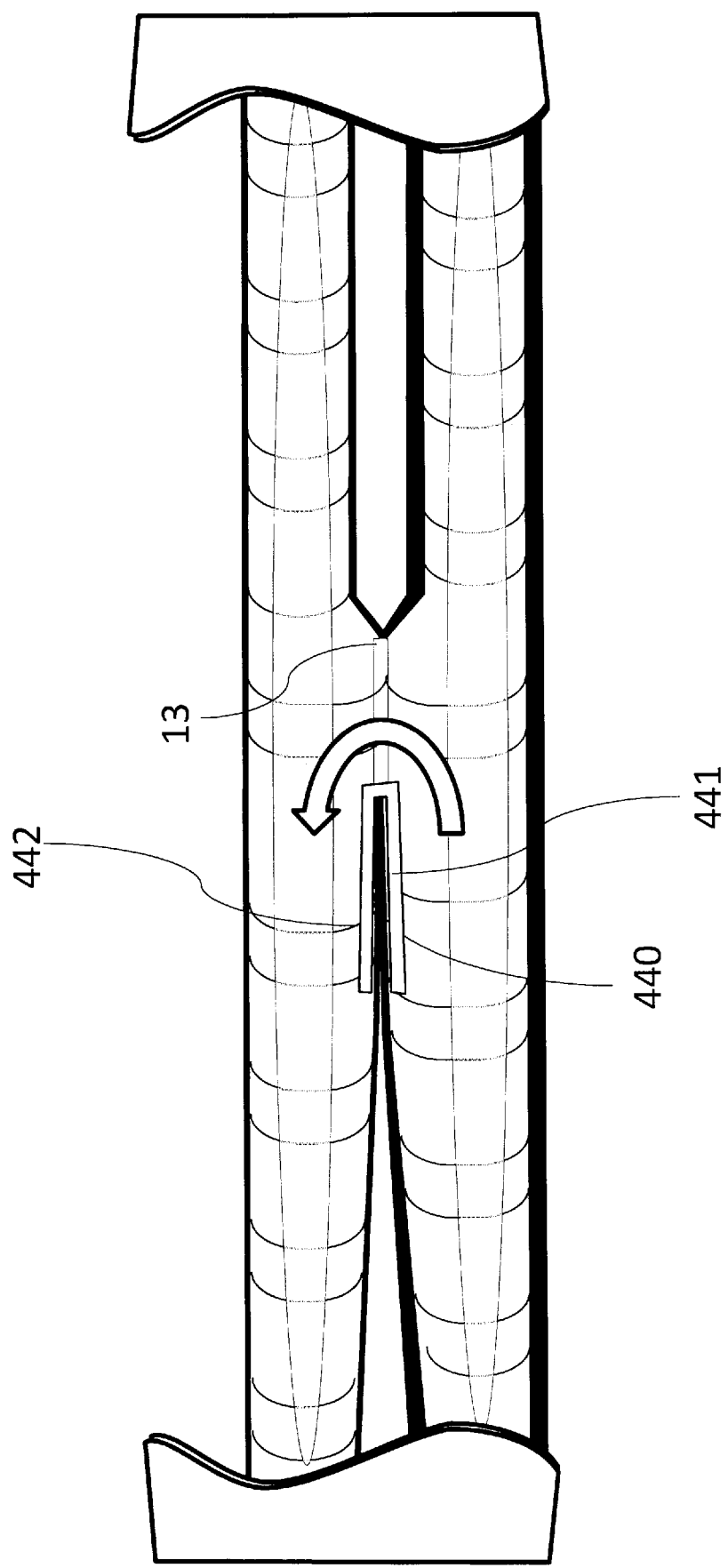
FIG. 25 is a view similar to FIGS. 18-24 showing the completed anastomosis with the mechanical fixation device holding the vessel walls and fascia such that the two blood vessels cannot separate appreciably and the outlet of the fascia is held open, after the remaining portions of the device have been withdrawn.

The implant clip 440 is configured to be removably disposed within the catheter assembly 460 for later deployment within the anastomosis 13 (see FIG. 26) to secure the side wall of the first blood vessel to the side wall of the second blood vessel. The implant clip 440 has opposing arms 441 and 442, which are generally parallel with one another when the implant is deployed. More particularly, the implant clip 440 defines a clamp volume between the first arm 441 and the second arm 442. As shown in FIG. 25, when the implant clip 440 is deployed, the first arm 44 is disposed in the first vessel 1 and the second arm 442 is disposed in the second vessel 2. Thus, the side wall of the first blood vessel 1 and the side wall of the second blood vessel 2 are within the clamp volume. As shown, the opposing surfaces of the first arm 461 and the second arm 462 include a set of grooves, ridges or structures 443 to improve the purchase between the implant clamp and the vessel walls. The arms 441, 442 are deployed such that they are each generally parallel to the axis of the vessels in which they are deployed and exert a pinching force to the vessel walls to bring them into approximation with one another. In some embodiments, the implant clip 440 is configured to deform from a first configuration (e.g., FIG. 13b) to a second configuration (e.g., FIG. 24). The first arm (or portion) 441 is spaced apart from the second arm (or portion) 442 by a first distance when the implant clip 440 is in the first configuration. The first arm (or portion) 441 is spaced apart from the second arm (or portion) 442 by a second distance when the implant clip 440 is in the second configuration. The implant clip is configured to exert a clamp force on the side wall of the first blood vessel 1 and the side wall of the second blood vessel 2 when the implant clip is in the first configuration. In some embodiments, the arms 461, 462 may be made of Nitinol® or other re-absorbable material such as Polylactic Acid (PLA) if only short term fixation is required. The deployment of the mechanical fixation implant utilizes plastic or elastic flexure of the device to ensure that both vessel walls are captured within the clamp volume.

In some embodiments, deployment and/or flexure of the implant clamp 440 is caused by movement of the actuator 470. As shown, the actuator 470 can be advanced into a space within the implant and between the implant arms 461, 462, as shown in FIG. 13a. The deployment element 471 on the distal end of the actuator 470 may be engageable with features 463 on the internal portions of the implant 460. The engagement of the deployment element 471 and these features 463 can provide a dual purpose—first to aid in deployment of the implant clip 460 and second to provide fixation to the vessel wall, thereby ensuring that the implant is secured to the vessel after deployment. In some embodiments, the deployment element 471 can comprise a helicoidal protrusion on the distal end of the shaft, and the features 463 comprise serrations on the inner surfaces of the arms 461, 462 which engage the helicoidal protrusion. In other embodiments, any suitable mechanism for engagement and deployment can be utilized.

Figure 14:
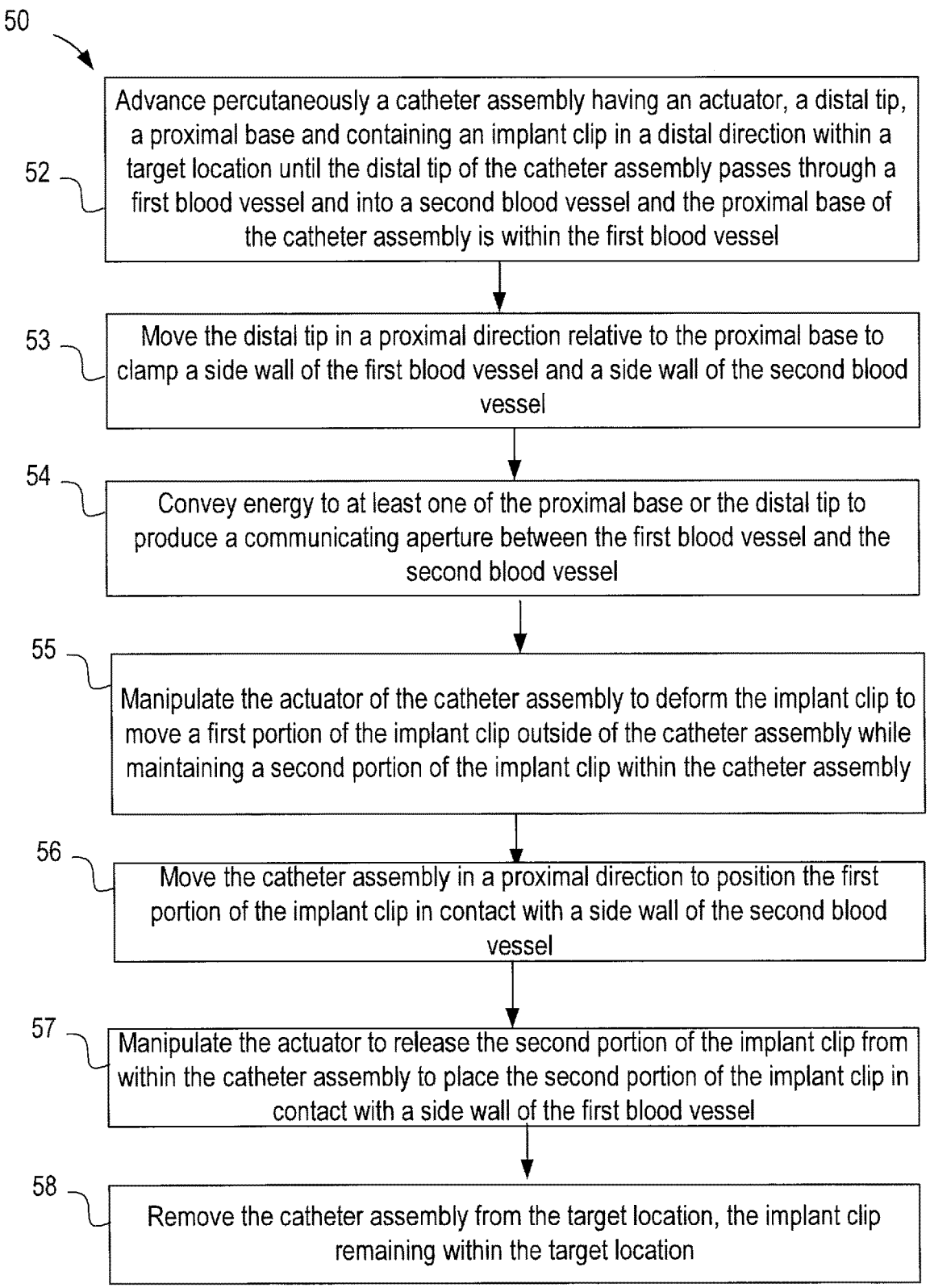
FIG. 14 is a flow chart of a method of percutaneously creating a fistula according an embodiment.

FIG. 14 is a flow chart of a method 50 of percutaneously creating a fistula according an embodiment. The method 50 is described in connection with schematic illustrations of FIGS. 15-26, which depict the creation of a fistula using the catheter assembly 460 and the implant clip 440. Although the method 50 is described as being performed with the catheter assembly 460 and the implant clip 440, in other embodiments, the method 50 is not limited to the specific instruments and devices shown in FIGS. 15-26, but can be performed using any suitable instruments and devices of the types shown and described herein. For example, although FIGS. 15-26 show the use of a single catheter assembly 460 to create a fistula and deploy the clamp 440, in other embodiments, the method 50 can be performed using multiple separate catheter assemblies.

Figure 15:
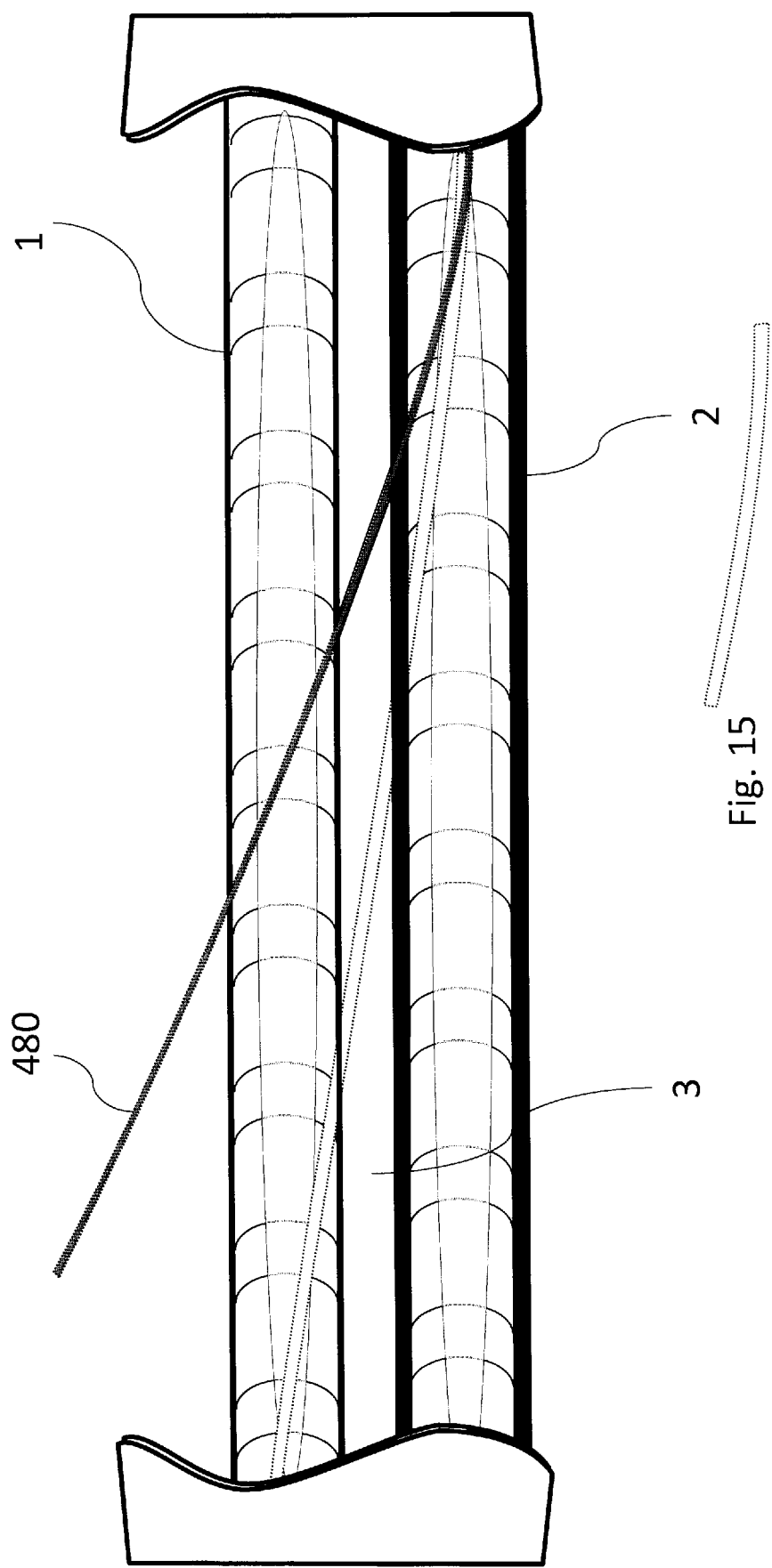
FIG. 15 illustrates two adjacent blood vessels wherein a guidewire has been placed through the first vessel, across a layer of fascia, and into the second blood vessel.
Figure 16:
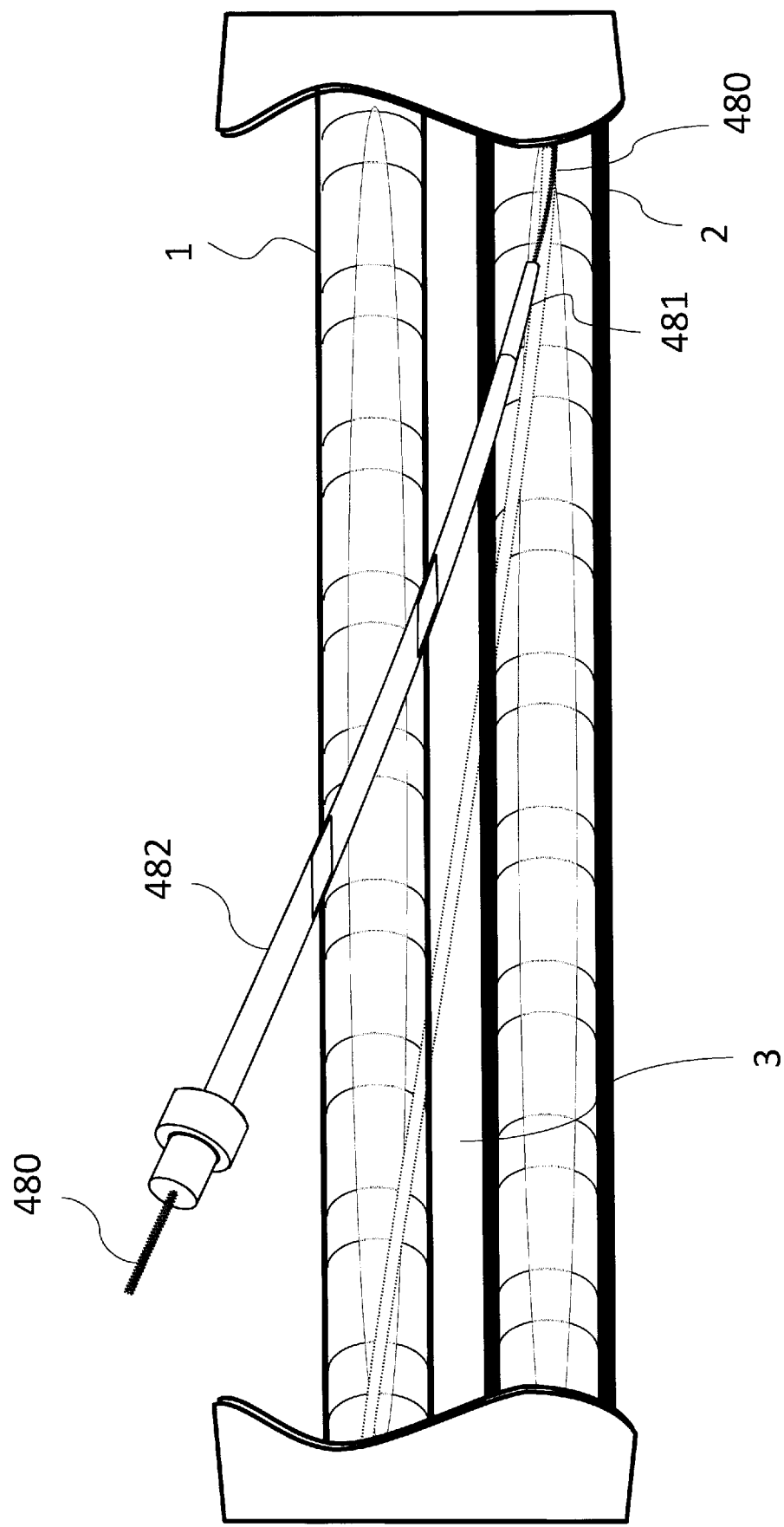
FIG. 16 is a view similar to FIG. 15 wherein a dilator and sheath have been placed over the guidewire.
Figure 17:
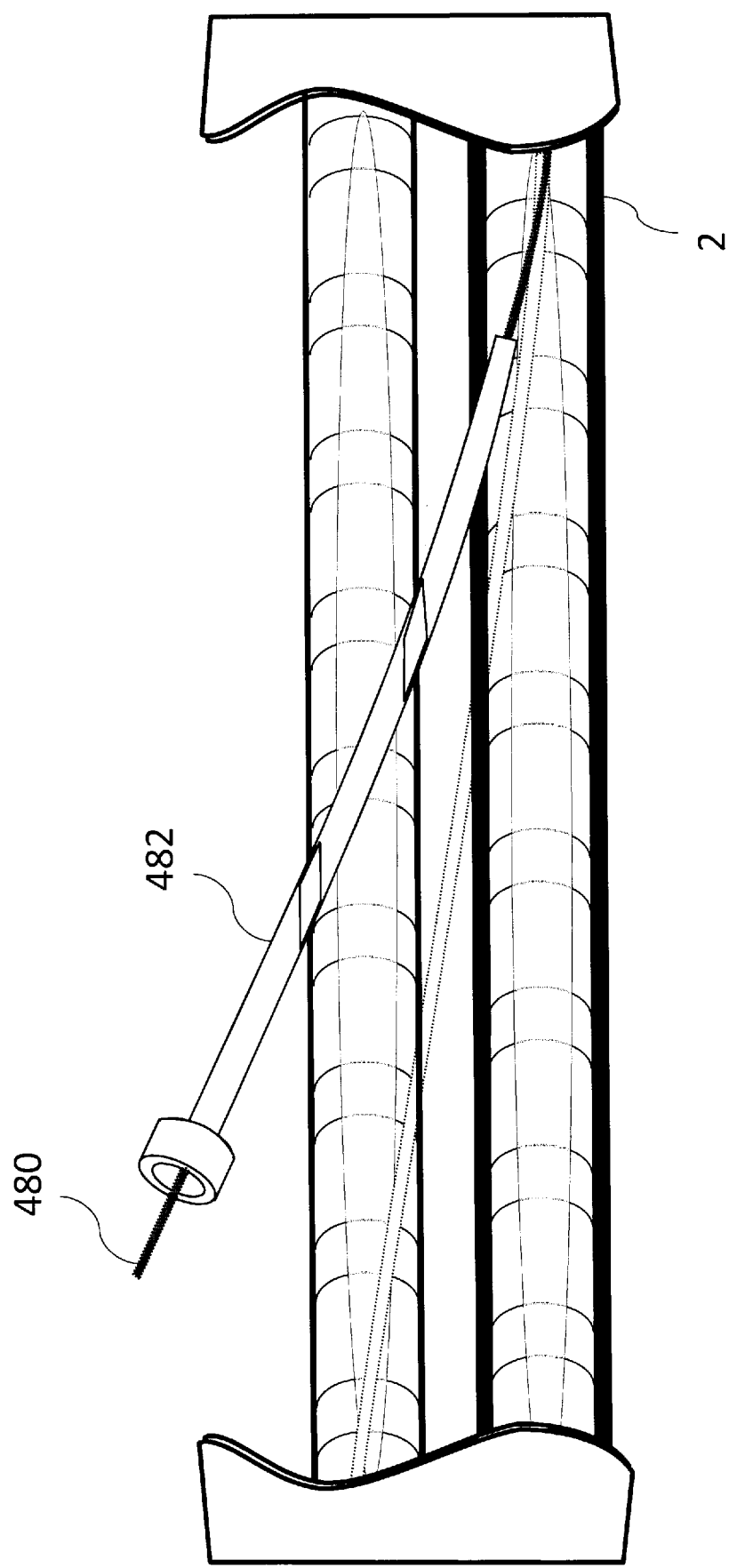
FIG. 17 is a view similar to FIGS. 15-16 showing the sheath and guidewire positioned to provide access to the second blood vessel.

FIGS. 15-17 show adjacent vessels 1, 2 in which an anastomosis is to be created. These figures show certain operations that can be performed apart from (or in advance of) performing the method 50. Specifically, shows a guidewire 480 that has been placed through the vessel (or vein) 1 and into the vessel (or artery) 2. In FIG. 16, a sheath 482 and dilator 481 are then placed over the guidewire 480 through the vein 1, across a layer of fascia 3, and into the artery 2. Then, as shown in FIG. 17, the sheath 482 and guidewire 480 are positioned to provide access to the artery 2.

Figure 18:
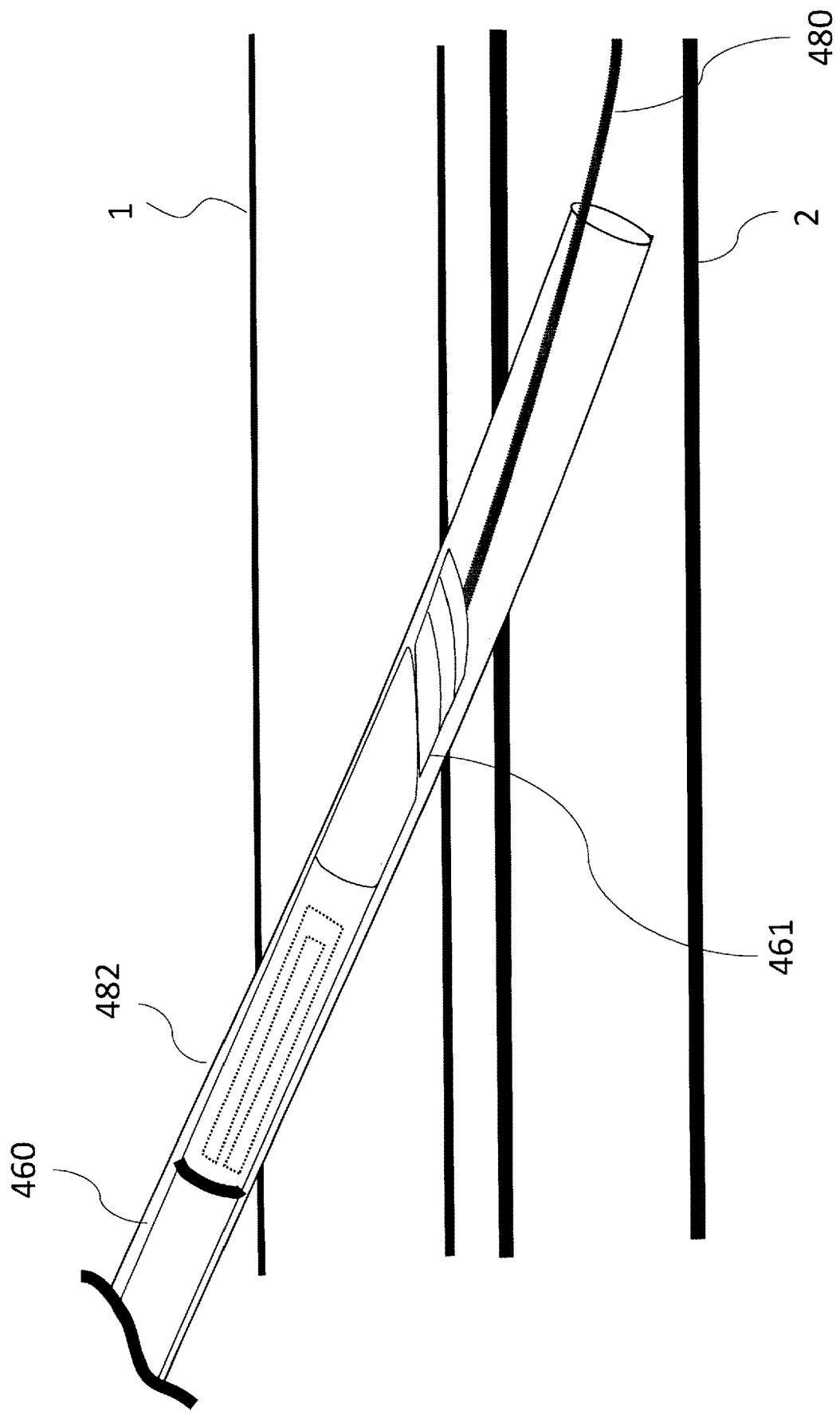
FIG. 18 is a schematic view showing the device of FIGS. 13, 13a and 13b being tracked over the guidewire through the sheath.
Figure 19:
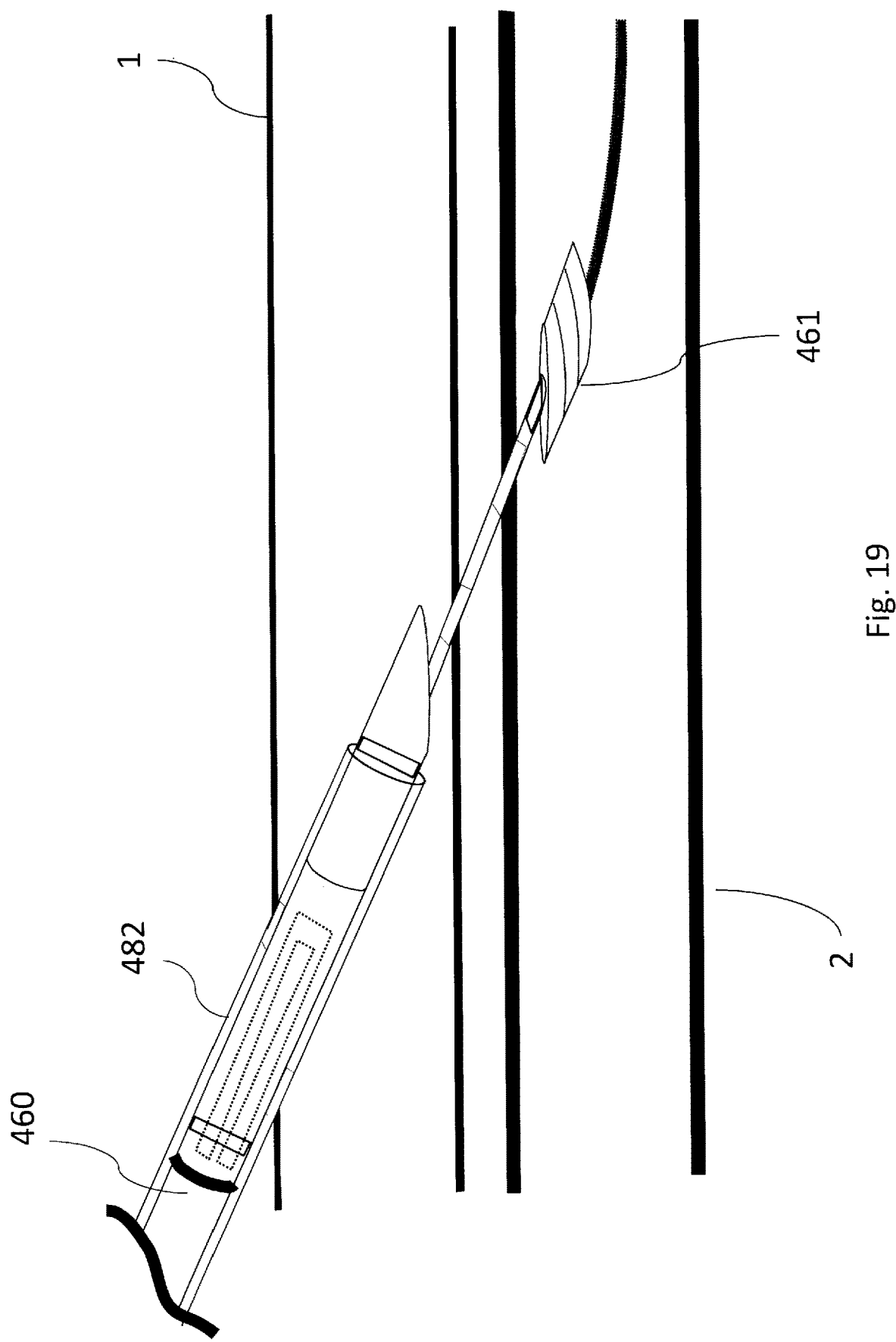
FIG. 19 is a view similar to FIG. 18 wherein the device has been positioned to utilize its anastomotic catheter for creating an anastomosis at the desired site, with the sheath having been retracted into the first blood vessel.

Referring to FIG. 14, the method 50 includes advancing percutaneously a catheter assembly having an actuator, a distal tip, a proximal base and containing an implant clip in a distal direction within a target location until the distal tip of the catheter assembly passes through a first blood vessel and into a second blood vessel and the proximal base of the catheter assembly is within the first blood vessel, at 52. The catheter assembly can be, for example, the catheter assembly 460 described herein. As shown in FIG. 18, the catheter 460 can be advanced through the sheath 482 over the guidewire 480. As shown in FIG. 19, the sliding distal tip 461 has been advanced into the artery 2, while the proximal portion 462 remains in the vein 1. In this manner, the catheter assembly 460 is positioned to create an anastomosis at a desired site (or target location) through the walls of the vein and artery. In some embodiments, the method can optionally include retracting the sheath 482 into the vein.

Figure 20:
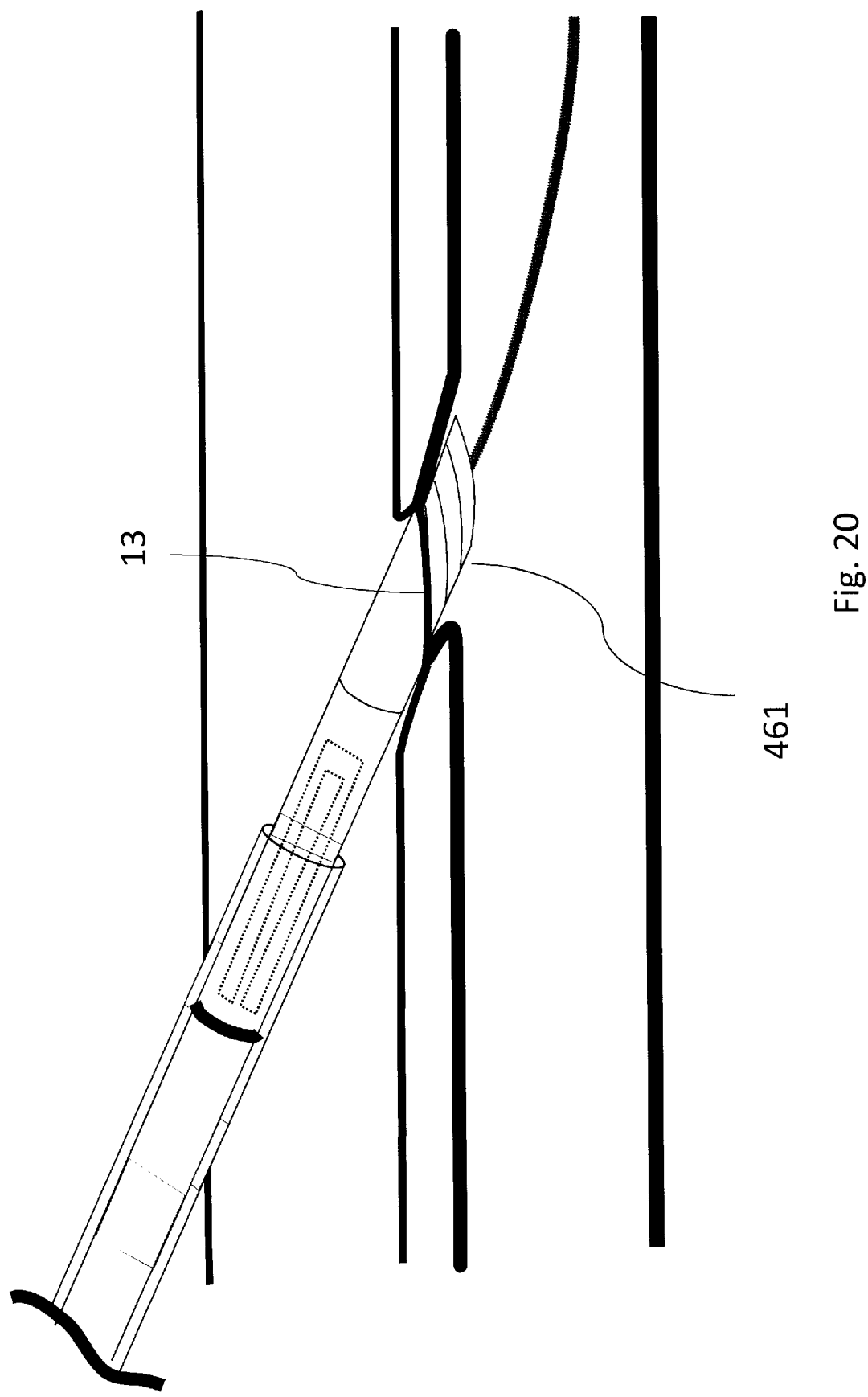
FIG. 20 is a view similar to FIGS. 18-19 wherein the anastomotic catheter has created an anastomosis at the desired location.
Figure 21:
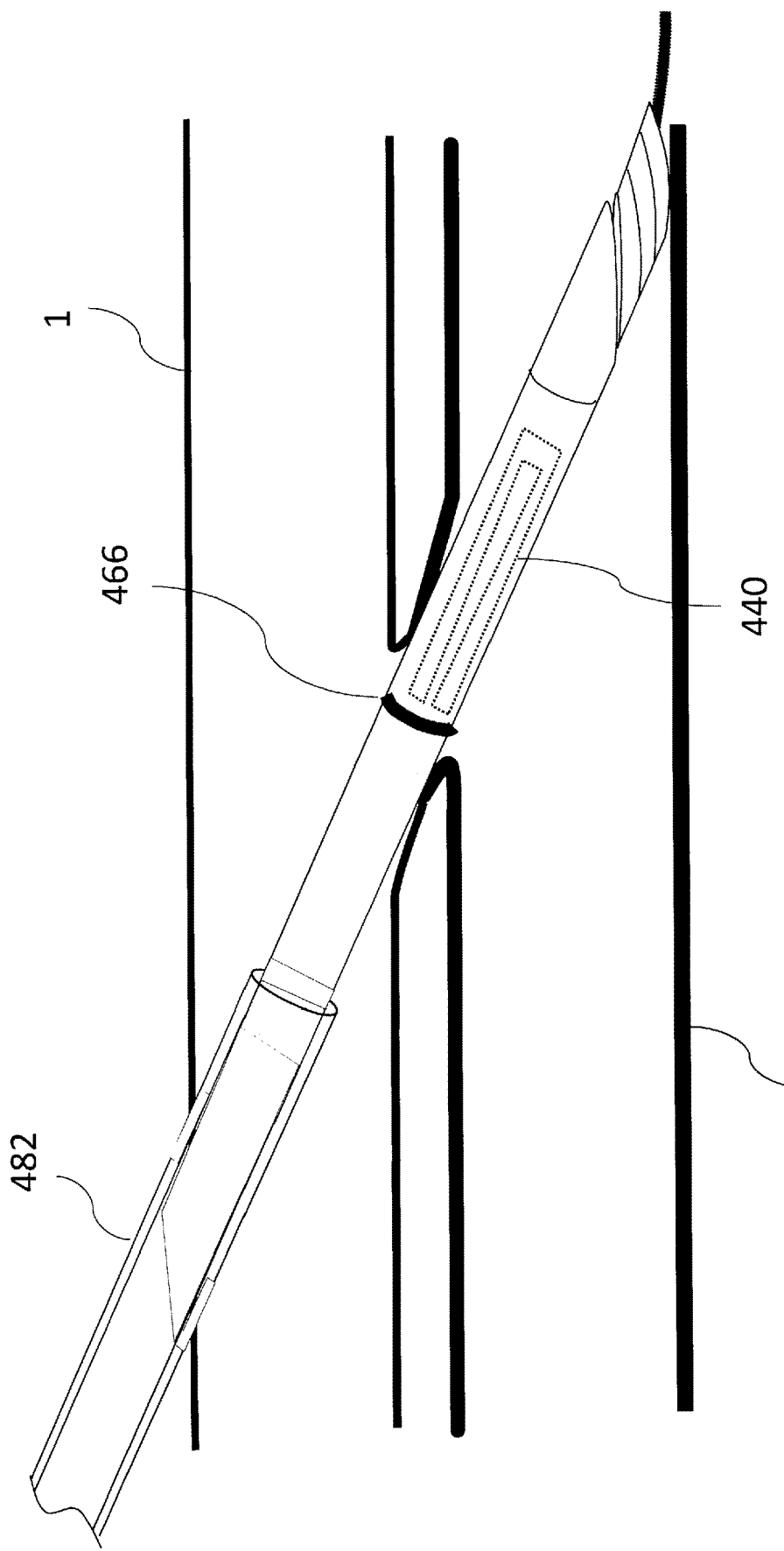
FIG. 21 is a view similar to FIGS. 18-20 wherein the deployment device has been advanced forward through the anastomosis after creation.

The distal tip of the catheter assembly is then moved in a proximal direction relative to the proximal base to clamp a side wall of the first blood vessel and a side wall of the second blood vessel, at 53. As shown in FIG. 20, the distal tip 461 has been retracted to clamp tissue at the procedural site between the distal tip 461 and the proximal portion 462 of the catheter 460. Energy is then conveyed to at least one of the proximal base or the distal tip to produce a communicating aperture 13 between the first blood vessel and the second blood vessel, at 54, in the manner described above in connection with the catheter assembly 160, to cut, form, and weld an anastomosis 13 between the vessels 1, 2.

In some embodiments, the method can optionally include repositioning or moving the catheter to align or position the implant clip 440 and/or the catheter bulkhead 464 in the desired position relative to the opening 13 between the vessels. For example, in FIG. 19, the catheter assembly 460 has been advanced distally through the anastomosis 13 after creation, while the sheath 882 maintains position. In some embodiments, the catheter assembly 460 includes an echogenic feature 466 used to aid in visualization during the positioning of the device.

Figure 22:
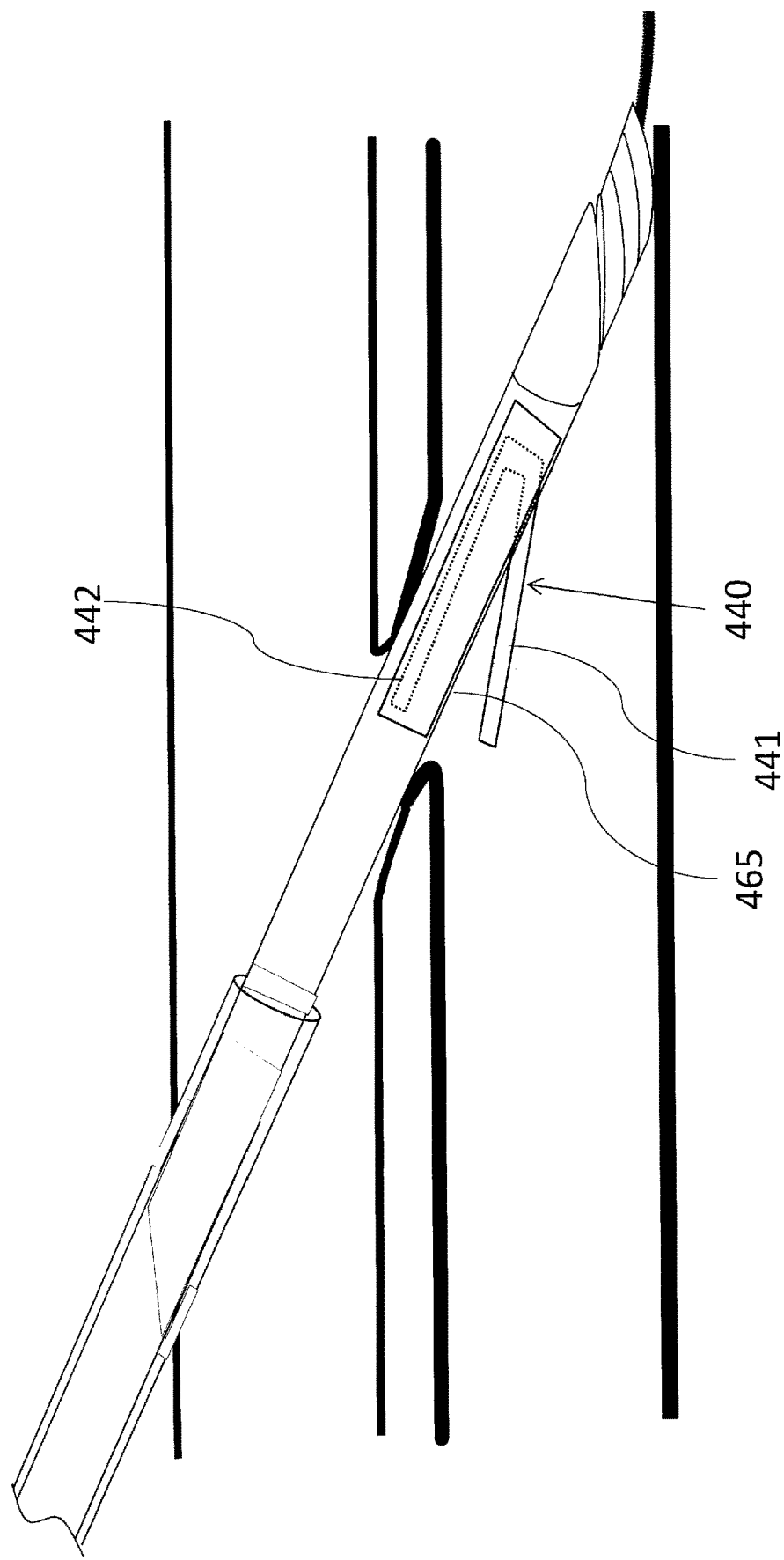
FIG. 22 is a view similar to FIGS. 18-21 wherein the mechanical fixation implant has been flexed open so that the vessel walls and fascia are captured within the mechanical fixation device.

The method 50 further includes manipulating the actuator of the catheter assembly to deform the implant clip to move a first portion (or arm) of the implant clip outside of the catheter assembly while maintaining a second portion (or arm) of the implant clip within the catheter assembly, at 55. Referring to FIG. 22, the implant clip 440 has been flexed open by the actuator 470 so that the vessel walls and fascia may be captured within the mechanical fixation device. Specifically, the first portion (or arm) 441 of the implant clip 441 is moved through a side opening 465 out of the catheter assembly 460. As described herein, in some embodiments, the first portion 441 can be deformed to expand the size of the clamp volume and urge the first portion 441 outside of the catheter assembly 460. As shown, the second portion 442 remains secured within the catheter assembly 460 (and/or the bulkhead 464). In some embodiments, for example, the actuator 470 can include a retention or release element that retains the second arm 442 while the actuator 470 urges the first arm 441 out of the catheter assembly 460 to be in position to engage the sidewall of the second blood vessel (or artery) 2.

Figure 23:
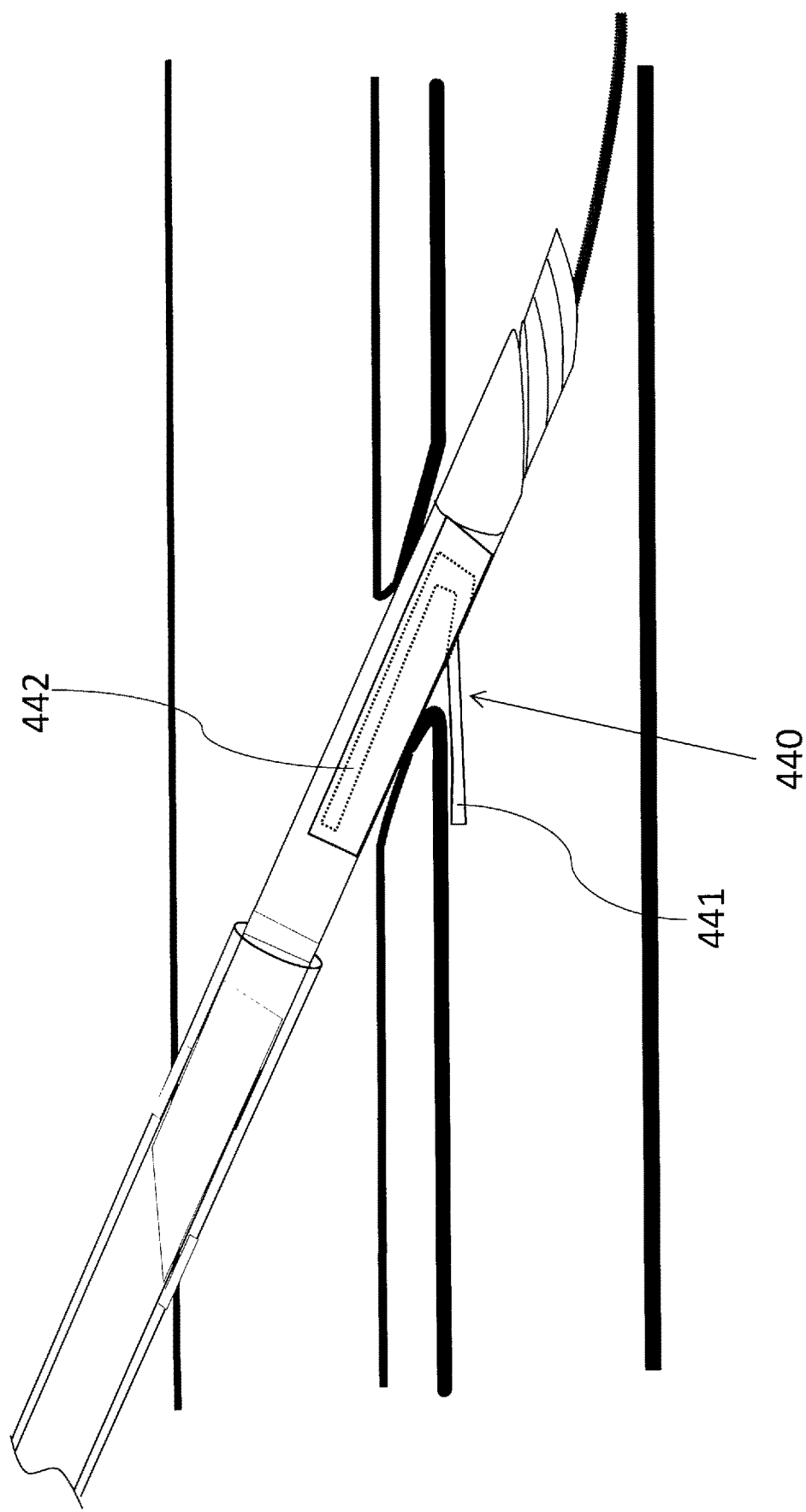
FIG. 23 is a view similar to FIGS. 18-22 wherein the delivery device has been retracted to position the mechanical fixation device.

The catheter assembly is then moved in a proximal direction to position the first portion (or arm) of the implant clip in contact with a side wall of the second blood vessel, at 56. As shown in FIG. 23, the catheter assembly 460 has been retracted (moved proximally) to position the implant clip 440 such that the first arm 461 is in contact with the side wall of the artery. In FIG. 24, the continued movement of the catheter assembly 460 cases the implant clip 440 to be fully engaged with the vessel side walls on one side of the anastomosis, for the purpose of fixing the vessel sidewalls together after the formation of the anastomosis.

The method further includes manipulating the actuator to release the second portion (or arm) of the implant clip from within the catheter assembly to place the second portion of the implant clip in contact with a side wall of the first blood vessel, at 57. In this manner, the second arm of the implant clip can be engaged with the side wall of the first blood vessel. Moreover, by releasing the second portion, the implant clip can return back towards its first configuration and apply the desired clamp force against the vessel side walls. FIG. 25 shows the anastomosis 13, with the implant clip 440 holding the vessel walls and fascia such that the vein and artery cannot separate appreciably and the outlet of the fistula is held open. FIG. 26 illustrates the anastomosis with the mechanical fixation device from a different perspective.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

For example, although described as being applicable to creating an arteriovenous (AV) fistula), the invention is applicable to any combination of vessels or tissues.

Figure 27:
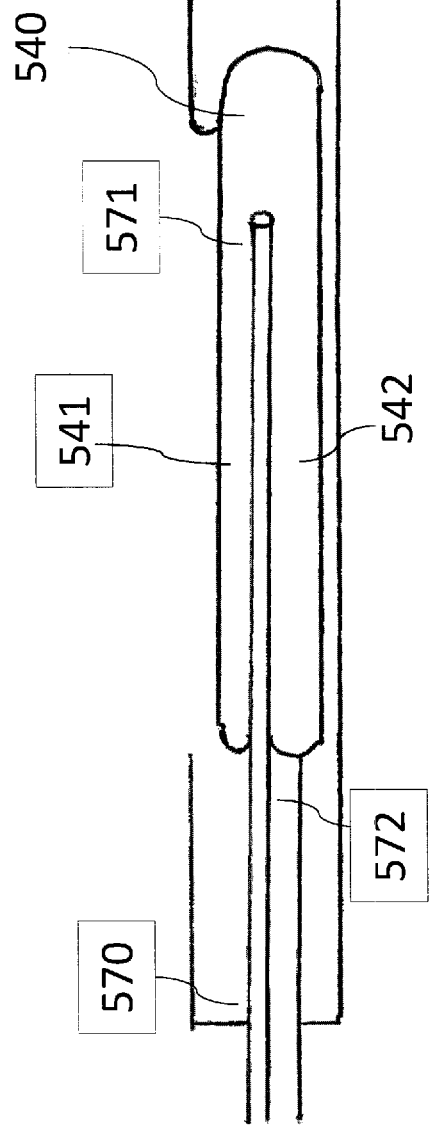
FIGS. 27 and 27a are schematic illustrations of an actuator according to an embodiment in a first configuration (FIG. 27) and a second configuration (FIG. 27a).
Figure 27A:
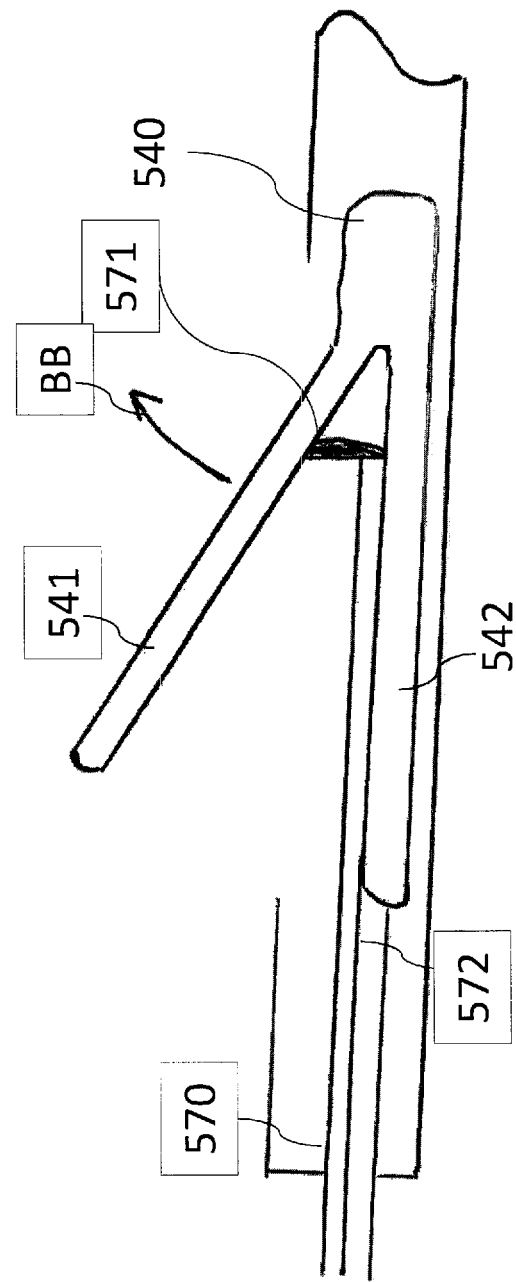

Although the actuator 470 is described as having a deployment element 471 that rotates or otherwise engages with the features 443 of the implant clip 440, in other embodiments, an actuator can include an expandable deployment element. For example FIGS. 27 and 27a show a schematic illustration of an actuator 570 that deploys and releases an implant clip 540. The actuator 570 includes a deployment element 571 and a release element 572. The clip 540 is similar to the clip 440 described above, and has a first portion (or arm) 541 and a second portion (or arm) 572. In use, the actuator 570 deploys the implant clip 540 by first expanding the deployment element 571 (as shown in FIG. 27a). In this manner, the deployment element 571 can exert a force on the first portion 541 to deform (or move) the first portion 541 out of the catheter assembly, as shown by the arrow BB in FIG. 27*a*. The deployment element 571 can be maintained in its expanded configuration during the positioning of the first portion 541 (and the clip) against the side wall of one of the vessels. When the first portion 541 is in position against the side wall of the vessel, the deployment element 571 can be moved (e.g., proximally) to allow the implant clip to return to its first (or normally closed) configuration (not shown). The implant clip 540 can then be positioned such that the second portion 542 is in its desired position. Then, the release element 572 can be moved to release the implant clip into position.

What is claimed is:

1. A method of percutaneously creating a fistula, comprising:
    inserting percutaneously a medical instrument to a target location having a first blood vessel and a second blood vessel;
    deploying, via the medical instrument, a fastener to the target location, the fastener being in a first configuration before the deploying, the fastener being in a second configuration after the deploying, the fastener limiting relative movement between the first blood vessel and the second blood vessel when in the second configuration; and
    producing percutaneously an anastomosis between the first blood vessel and the second blood vessel;
    wherein: the medical instrument includes a needle; the fastener is a flexible member attached to the needle; and the deploying includes:
    advancing the needle within the target location to surround at least a portion of each of the first blood vessel and the second blood vessel with a portion of the flexible member;
    fixating a first end of the flexible member to a first portion of skin outside of the target location; and
    fixating a second end of the flexible member to a second portion of skin outside of the target location.

2. The method of claim 1, wherein:
    the deploying the fastener causes relative movement between the first blood vessel and the second blood vessel to place a side wall of the first blood vessel into engagement with a side wall of the second blood vessel; and
    the side wall of the first blood vessel being maintained in engagement with the side wall of the second blood vessel after the deploying.

3. The method of claim 1, wherein the flexible member includes one of a suture or a sling.

4. The method of claim 3, wherein the fixating the first end of the flexible member includes at least one of forming a knot in the first end, applying a fixation element to the first end, or applying an adhesive to the first end.

5. The method of claim 1, wherein the advancing the needle within the target location includes changing a curvature of the needle.

6. The method of claim 5, wherein the needle is constructed from a shape memory material.

7. The method of claim 5, wherein:
    the medical instrument includes an introducer;
    the inserting the medical instrument including inserting a tip of the introducer, the needle being within a lumen of the introducer to maintain the needle in a first shape before the deploying the flexible member; and
    the advancing the needle includes moving the needle out of the lumen of the introducer, the needle transitioning to a second shape when moved out of the lumen.

8. The method of claim 7, wherein the tip of the introducer includes a beveled surface, the method further comprising:
    rotating the introducer, before the advancing the needle, to align the beveled surface towards the first blood vessel.

9. The method of claim 7, wherein:
    the first shape is substantially linear and the second shape is curved;
    the needle deforms about a predetermined bend axis when the needle is moved out of the lumen; and
    the needle includes an alignment feature that is matingly received within the lumen of the introducer, the alignment feature being aligned with the predetermined bend axis.

10. The method of claim 1, wherein the producing the anastomosis includes:
    extending the needle through a side wall of the first blood vessel and a side wall of the second blood vessel to produce a communicating aperture between the first blood vessel and the second blood vessel.

11. A method of percutaneously creating a fistula, comprising:
    inserting percutaneously a medical instrument to a target location having a first blood vessel and a second blood vessel;
    deploying, via the medical instrument, a fastener to the target location, the fastener being in a first configuration before the deploying, the fastener being in a second configuration after the deploying, the fastener limiting relative movement between the first blood vessel and the second blood vessel when in the second configuration; and
    producing percutaneously an anastomosis between the first blood vessel and the second blood vessel;
    wherein the producing the anastomosis includes:
    positioning a distal end of a catheter assembly to engage an inner surface of a side wall of the first blood vessel, the catheter assembly being different from the medical instrument; and
    extending a piercing member from the distal end of the catheter assembly, through the side wall of the first blood vessel and a side wall of the second blood vessel to produce a communicating aperture between the first blood vessel and the second blood vessel; wherein:
    the medical instrument includes a needle and an introducer;
    the fastener is a flexible member attached to the needle;
    the deploying is performed before the producing the anastomosis and includes:
    advancing the needle within the target location such that a portion of the flexible member surrounds at least a portion of each of the first blood vessel and the second blood vessel;
    applying a tension force to the flexible member to move the side wall of the first blood vessel into engagement with the side wall of the second blood vessel; and
    fixating a first end of the flexible member and a second end of the flexible member to skin outside the target location to maintain engagement between the side wall of the first blood vessel and the side wall of the second blood vessel after the deploying.

12. A method for creating a percutaneous fistula, comprising:
    selecting an appropriate procedural site having each of a first blood vessel and a second blood vessel in close proximity to one another;
    securing the first and second blood vessels together using a mechanical fastener; and creating an anastomosis between the first and second blood vessels;

wherein the mechanical fastener comprising a curved needle and the securing step comprising inserting the curved needle percutaneously to the procedural site and positing the curved needle to extend around each of the two blood vessels and thereby secure them together;

wherein the curved needle is inserted through a lumen of a primary needle; and wherein the curved needle is attached to a length of suture, and the curved needle is used to advance the length of suture so that the length of suture is wrapped about the first and second blood vessels, the method further comprising fixating an end of the length of suture to a portion of skin and tension the suture to approximate and hold the blood vessels in place.

13. The method as recited in claim 12, and further comprising a step of fixating a second end of the length of suture to a second portion of skin.

14. The method as recited in claim 12, wherein the step of creating an anastomosis occurs before or after the step of securing the first and second blood vessels together using a mechanical fastener.

\* \* \* \* \*